US011237175B2

(12) United States Patent
Granier et al.

(10) Patent No.: US 11,237,175 B2
(45) Date of Patent: Feb. 1, 2022

(54) EARLY PREDICTION MARKERS OF DIABETIC NEPHROPATHY

(71) Applicants: BIO-RAD EUROPE GMBH, Basel (CH); CENTRE NATIONAL DE LA RECHERCHE SCIENTIFIQUE, Paris (FR); UNIVERSITE DE MONTPELLIER, Montpellier (FR); CHU MONTPELLIER, Montpellier (FR)

(72) Inventors: Claude Granier, Istres (FR); Franck Molina, Les Matelles (FR); Nicolas Salvetat, Montpellier (FR); Laurence Molina, Las Matelles (FR); Randa Siala, Brussels (BE); Eric Renard, Saint Clement de Riviere (FR)

(73) Assignees: BIO-RAD EUROPE GMBH, Basel (CH); CENTRE NATIONAL DE LA RECHERCHE SCIENTIFIQUE, Paris (FR); UNIVERSITÉ DE MONTPELLIER, Montpellier (FR); CHU MONPELLIER, Montpellier (FR)

( * ) Notice: Subject to any disclaimer, the term of this patent is extended or adjusted under 35 U.S.C. 154(b) by 268 days.

(21) Appl. No.: 15/322,742

(22) PCT Filed: Jun. 30, 2015

(86) PCT No.: PCT/EP2015/064831
§ 371 (c)(1),
(2) Date: Dec. 29, 2016

(87) PCT Pub. No.: WO2016/001215
PCT Pub. Date: Jan. 7, 2016

(65) Prior Publication Data
US 2017/0153249 A1 Jun. 1, 2017

(30) Foreign Application Priority Data
Jul. 1, 2014 (EP) .................................... 14306071

(51) Int. Cl.
*G01N 33/53* (2006.01)
*G01N 33/68* (2006.01)
*G01N 27/447* (2006.01)

(52) U.S. Cl.
CPC ... *G01N 33/6893* (2013.01); *G01N 27/44778* (2013.01); *G01N 33/6848* (2013.01); *G01N 2800/042* (2013.01); *G01N 2800/347* (2013.01); *G01N 2800/50* (2013.01)

(58) Field of Classification Search
CPC ......... G01N 33/6893; G01N 27/44778; G01N 33/6848; G01N 2800/50; G01N 2800/042; G01N 2800/347
See application file for complete search history.

(56) References Cited

U.S. PATENT DOCUMENTS

| 9,134,326 | B2 * | 9/2015 | Jacobs | ............... G01N 33/6893 |
| 2006/0029956 | A1 | 2/2006 | Beyer et al. | |
| 2012/0034240 | A1 | 2/2012 | Kas et al. | |
| 2012/0329071 | A1 | 12/2012 | Chance et al. | |
| 2015/0072360 | A1 * | 3/2015 | Everett | ............... G01N 33/6893 435/7.92 |
| 2016/0169910 | A1 * | 6/2016 | Sever | ................. G01N 33/6827 435/7.92 |

FOREIGN PATENT DOCUMENTS

CN        101014862        8/2007

OTHER PUBLICATIONS

CA1 ELISA (2006, retrieved from https://cdn.mybiosource.com/tds/protoco_manuals/000000-799999/MBS762175.pdf).*
Lemoine et al (Expert review in Proteomics;2012,12(4) p. 333-342.*
Parker et al. (Molecular oncology;2014;8 pp. 840-858).*
O'Brien et al (Diabetes Care;1995, 1602-1605.*
Watts et al (Journal of the British Diabetic Association, vol. 6, Issue: 9, pp. 787-792.*
Kohler et al, Proteomics Clin. Appl;2010, 4,568-576.*
Strippoli et al (J. Am Soc Mephrol;2006, 17:S153-5.*
Afkarian, M. et al. "Optimizing a Proteomics Platform for Urine Biomarker Discovery" *Molecular and Cellular Proteomics*, Oct. 2010, pp. 2195-2204, vol. 9, No. 10.
Bellei, E. et al. "Proteomic analysis of early urinary biomarkers of renal changes in type 2 diabetic patients" *Proteomics Clinical Applications*, 2008, pp. 478-491, vol. 2.
Cho, E. et al. "The discovery of biomarkers for type 2 diabetic nephropathy by serum proteome analysis" *Proteomics Clinical Applications*, 2007, pp. 352-361, vol. 1.

(Continued)

*Primary Examiner* — Carmencita M Belei
(74) *Attorney, Agent, or Firm* — Saliwanchik, Lloyd & Eisenschenk

(57) ABSTRACT

The present invention concerns a method for the in vitro detection of an increased risk of diabetic nephropathy in a subject suffering from diabetes and being normoalbuminuric. Another aspect of the invention pertains to a method for the in vitro identification of a marker for prediction of diabetic nephropathy. Finally, the invention concerns a kit comprising means for detecting at least two proteins selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AMBP and zinc-alpha-2-glycoprotein.

7 Claims, 7 Drawing Sheets

(56) References Cited

OTHER PUBLICATIONS

Conde-Knape, K. "Heparan sulfate proteoglycans in experimental models of diabetes: a role for perlecan in diabetes complications" *Diabetes Metabolism Research and Reviews*, Jan. 1, 2001, pp. 412-421, vol. 17, No. 6.

Jin, J. et al. "Differential Proteome Profiling Using iTRAQ in Microalbuminuric and Normoalbuminuric Type 2 Diabetic Patients" *Experimental Diabetes Research*, 2012, pp. 1-31, vol. 2012, Article ID 168602.

Lacquaniti, A. et al. "'Normoalbuminuric' diabetic nephropathy: tubular damage and NGAL" *Acta Diabetologica*, Jun. 11, 2013, pp. 935-942, vol. 50, No. 6.

Lim, S. C. et al. "Adipocytokine zinc $\alpha_2$ glycoprotein (ZAG) as a novel urinary biomarker for normo-albuminuric diabetic nephropathy" *Diabetic Medicine*, Jun. 19, 2012, pp. 945-949, vol. 29, No. 7.

Nielsen, S. E. et al. "Urinary Liver-Type Fatty Acid-Binding Protein Predicts Progression to Nephropathy in Type 1 Diabetic Patients" *Diabetes Care*, Feb. 25, 2010, pp. 1320-1324, vol. 33, No. 6.

O'Brien, S. F. et al. "Exercise Testing as a Long-Term Predictor of the Development of Microalbuminuria in Normoalbuminuric IDDM Patients" *Diabetes Care*, Dec. 1, 1995, pp. 1602-1605, vol. 18, No. 12.

Otu, H. H. et al. "Prediction of Diabetic Nephropathy Using Urine Proteomic Profiling 10 Years Prior to Development of Nephropathy" *Diabetes Care*, Mar. 2007, pp. 638-643, vol. 30, No. 3.

Rao, P. V. et al. "Proteomic Identification of Urinary Biomarkers of Diabetic Nephropathy" *Diabetes Care*, Mar. 2007, pp. 629-637, vol. 30, No. 3.

Rossing, K. et al. "Urinary Proteomics in Diabetes and CKD" *Journal of the American Society of Nephrology*, Apr. 30, 2008, pp. 1-8.

Sharma, K. et al. "Two-dimensional fluorescence difference gel electrophoresis analysis of the urine proteome in human diabetic nephropathy" *Proteomics*, 2005, pp. 2648-2655, vol. 5.

Soggiu, A. et al. "A discovery-phase urine proteomics investigation in type 1 diabetes" *Acta Diabetologica*, Jun. 8, 2012, pp. 453-464, vol. 49, No. 6.

Zürbig, P. et al. "Urinary Proteomics for Early Diagnosis in Diabetic Nephropathy" *Diabetes*, Aug. 7, 2012, pp. 1-10.

Written Opinion in International Application No. PCT/EP2015/064831, dated Dec. 18, 2015, pp. 1-12.

European Search Report in Application No. 14306071.3, dated Feb. 17, 2015, pp. 1-14.

Liu, H. et al. "Use of Detection of α1-Myoglobin and Albumin of Urine after Exercise in the Early Diagnosis of Diabetic Nephropathy" *Occupation and Health*, Oct. 2004, pp. 1-5, vol. 20, No. 10.

\* cited by examiner

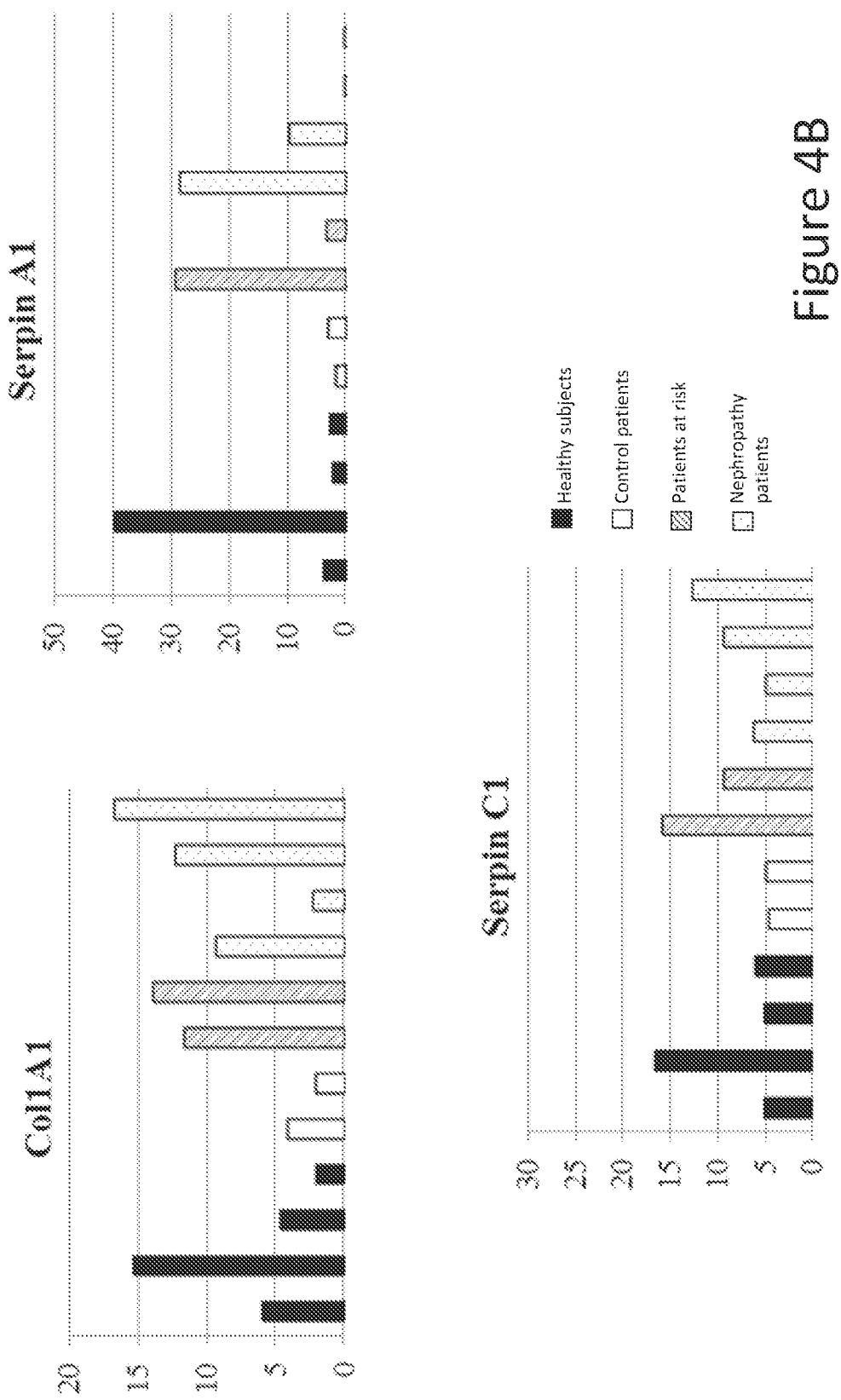

EARLY PREDICTION MARKERS OF DIABETIC NEPHROPATHY

CROSS-REFERENCE TO RELATED APPLICATION

This application is the U.S. national stage application of International Patent Application No. PCT/EP2015/064831, filed Jun. 30, 2015.

The invention pertains to the technical domain of prediction of diabetic nephropathy.

Diabetes is characterized by an abnormally high level of glucose in blood. Type 1 diabetes (IDDM: insulin-dependent diabetes mellitus) is caused by the destruction of the pancreas β-cells of the islets of Langerhans, and usually leads to an absolute insulin deficiency. Type 2 diabetes (NIDDM: non-insulin-dependent diabetes mellitus) is characterized by an abnormal insulin resistance, which can be associated with insulinopenia. Diabetic nephropathy (DN) is a glomerular pathology affecting diabetic patients. DN affects about 25-40% of type 1 or type 2 diabetic patients and is the major cause of end-stage renal disease (ESRD) in these patients. Diabetic nephropathy is characterized by an alteration of the glomerular filtration rate and progressive abnormal increase of proteins in the urine. Microalbuminuria (urine albumin excretion is about 30-300 mg/24 h) is the first clinical sign of early DN and has been the standard test for diagnosing DN. The microalbuminuria stage may last about 10 years. Then, the amount of urine albumin increases above 300 mg/24 h (macroalbuminuria) which is indicative of overt DN and increased risk of ESRD.

Several studies have used differential proteomic approaches for searching for new markers for diagnosing DN. Generally, such studies are based on the comparison of urine proteomes of diabetic patients with DN with control subjects (healthy subjects or diabetic patients without DN).

Sharma et al. (Proteomics 2005, 5, 2648-2655) showed with a bidimensional differential in-gel electrophoretic analysis (2D DIGE) that alpha 1 antitrypsin (AAT) is increased in urine samples of diabetic patients with advanced DN displaying a macroalbuminuria compared to healthy subjects.

In another study (Rao et al., Diabetes Care 30:629-637, 2007) a comparison was done by 2D DIGE associated with protein identification using LC-MS/MS between urine proteomes of type 2 diabetic patients with normoalbuminuria, microalbuminuria or macroalbuminuria, and with control subjects. Seven proteins were found as being expressed in higher relative abundance and four proteins in lower relative abundance in DN macroalbuminuric patients compared to normoalbuminuric diabetic patients.

Cho et al. (Proteomics Clin. Appl. 2007, 1, 352-361) tested serum proteomes of type 2 diabetic patients with normoalbuminuria and with microalbuminuria with bidimensionnel gel electrophoresis (2D-GE) and ESI-Q-TOF MS/MS. The authors identified a panel of 18 protein spots down-regulated or up-regulated in microalbuminuric patients compared to normoalbuminuric, and they suggested that the protein DBP (vitamin D binding protein) may be a diagnostic marker of type 2 DN.

In Bellei et al. (Proteomics Clin. Appl. 2008, 2, 478-491) 2D-GE separation followed by ESI-Q-TOF MS/MS identification permitted to find 15 proteins differently expressed in urine of normoalbuminuric patients with type 2 diabetes mellitus and patients with type 2 diabetes mellitus having DN and displaying microalbuminuria compared to healthy subjects.

Afkarian et al. (Molecular & Cellular Proteomics 9:2195-2204, 2010) experimented with different protocols of sample processing of frozen urine before iTRAQ (Isobaric tags for relative and absolute quantification)-based proteomics approach on samples from healthy volunteers. A list of 37 proteins differentially expressed between the DN macroalbuminuric patients and the diabetic normoalbuminuric patients without DN was shown.

Jin et al. (Experimental Diabetes Research, Vol. 2012, Article ID 168602) used the iTRAQ approach in normoalbuminuric and microalbuminuric diabetic patients and identified 193 proteins differentially expressed. After a selection and subsequent validation by Western blot and MRM, 3 proteins (Alpha 1 Antitrypsin, Alpha-1 acid glycoprotein 1 and Prostate Stem Cell Antigen) were considered as good biomarkers of DN.

Rossing et al. (J Am Soc Nephrol, 2008) identified by Capillary Electrophoresis-Mass Spectrometry (CE-MS) analysis a panel of biomarkers (mainly fragments of collagen type I and fragments of uromodulin) differently expressed in urine of diabetic patients with or without DN and found that the panel would allow to distinguish diabetic patients who had microalbuminuria who progressed toward overt DN (i.e. macroalbuminuria). Hence such biomarkers could be qualified as markers of prediction of DN development in patients with microalbuminuria. However the publication gives no data about predictive markers in normoalbuminuric patients.

Since the biomarkers identified in the above-mentioned studies were all only observed in patients already displaying an increased level of urine albumin (i.e. the differential expression is observed when DN, or at least with the early stage of DN, is already established), they can only have an interest for diagnostic purposes, particularly to confirm a diagnosis of DN, determined for example by the detection of a high level of urine albumin.

However, no indication can be deduced from these studies as to the predictive value of such biomarkers of the onset of DN in normoalbuminuric patients. Therefore, there is still a need to provide early prediction markers of DN that would permit the prediction of the onset of DN in diabetic patients who do not yet display any abnormal albuminuria.

Some previous experimental approaches aimed to identify markers of the prediction of DN.

Otu et al. (Diabetes Care, Volume 30, Number 3, March 2007) studied a retrospective cohort of diabetic patients that were followed up during 10 years. Proteome of urine samples taken in diabetic normoalbuminuric patients who remained normoalbuminuric during the follow-up was compared to the one of samples taken in normoalbuminuric patients who subsequently developed DN. Peaks corresponding to several peptides were identified as differentially expressed in the two groups and a subset of 12 peaks was defined as a predictive peak signature, allowing the prediction of DN. However to the inventors' knowledge, the corresponding proteins were not further characterized, and no prediction marker was indeed identified.

More recently, an approach using capillary electrophoresis mass spectrometry (CE-MS) highlighted a specific profile of 273 low-molecular weight peptides in urine for early diagnosis of diabetic nephropathy (Zurbig et al., Diabetes, 2012). Urine samples from a longitudinal cohort of type 1 and 2 diabetic patients were examined using a previously generated chronic kidney disease (CKD) biomarker classifier (CKD273 classifier) to assess peptides of collected urine for signs of DN. The application of the CKD273 classifier to samples of normoalbuminuric subjects up to 5 years prior to development of macroalbuminuria enabled early detection of subsequent progression to macroalbuminuria compared with urinary albumin routinely used to determine the diagnosis. While the article suggests that the CDK273 classifier "as a whole" could permit to identify normoalbuminuric patients who will develop DN, no hint is given about the potential predictive value, if any, of each of the individual components of the classifier.

It appears from the foregoing that still very few data exist on individual markers for the early prediction of DN in diabetic patients, in particular in normoalbuminuric diabetic patients.

The inventors were able to identify new DN prediction biomarkers in normoalbuminuric diabetic patients who were considered to be at risk of developing diabetic nephropathy on the basis of the test described in O'Brien et al. (1995). The present invention indeed relies on the surprising finding that a differential expression of certain proteins can be detected between patients determined to be at risk of developing DN according to the O'Brien test and patients determined not to be at risk of developing DN according to the O'Brien test, and that this variation is associated with the risk of developing diabetic nephropathy.

The present invention thus concerns a method for the in vitro detection of an increased risk of diabetic nephropathy in a subject suffering from diabetes and being normoalbuminuric, said method comprising the steps of:

(a1) measuring the level of at least one protein selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AM BP and zinc-alpha-2-glycoprotein in a biological sample taken from the subject, and (b) determining from the level measured at step (a1) if said subject has an increased risk of developing diabetic nephropathy.

Another aspect of the invention pertains to a method for the in vitro identification of a marker for prediction of diabetic nephropathy, said method comprising the steps of:

(a) determining the level of a protein in a biological sample taken from a subject suffering from diabetes who has been determined to be at risk of developing diabetic nephropathy, said biological sample being taken after said subject was subjected to a physical exercise, (b) determining the level of said protein in a biological sample taken from a subject suffering from diabetes who has been determined not to be at risk of developing diabetic nephropathy, said biological sample being taken after said subject was subjected to a physical exercise, (c) comparing the level determined at step (b) with the level determined at step (a), and (d) identifying said protein as being a marker for prediction of diabetic nephropathy if the levels compared at step (c) are different.

Another object of the invention is a kit comprising, in separate containers or in a same container, means for detecting at least two proteins selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AMBP and zinc-alpha-2-glycoprotein.

DESCRIPTION OF THE INVENTION

Definitions

A "subject" herein refers to any animal, such as a vertebrate or a mammal, preferably a non-human or human mammal. Examples of vertebrates include birds and poultry, in particular chickens. Examples of non-human mammals include rodents, horses, swine and primates. Most preferably, the subject is a human.

The "subject" according to the invention is an individual who suffers from diabetes, i.e. diabetes has been diagnosed in said individual.

"Diabetes mellitus", or "diabetes", refers to metabolic diseases characterized by an abnormally high level of glucose in blood, either because the pancreas does not produce enough insulin, or because cells do not respond to the insulin that is produced. There are two main types of diabetes.

Type-1 diabetes is caused by the destruction of the pancreatic β-cells of the islets of Langerhans, resulting in a failure to produce insulin, and it usually leads to an absolute insulin deficiency. It generally requires the subject to inject insulin or wear an insulin pump. This form is also referred to as "insulin-dependent diabetes mellitus" (IDDM) or "juvenile diabetes".

Type-2 diabetes is characterized by an abnormal insulin resistance, a condition in which cells fail to use insulin properly, sometimes combined with an absolute insulin deficiency. This form is also referred to as "non-insulin-dependent diabetes mellitus" (NIDDM) or "adult-onset diabetes".

The "subject" according to the invention may suffer from type-1 or type-2 diabetes. Preferably, the subject according to the invention suffers from type-1 diabetes.

"Diabetic nephropathy" (DN) is a glomerular pathology affecting diabetic patients. DN affects about 25-40% of type 1 or type 2 diabetic patients and is the major cause of end-stage renal disease (ESRD) in these patients. Diabetic nephropathy is characterized by an alteration of the glomerular filtration rate and progressive abnormal increase of proteins in the urine.

The first clinical sign of early DN is "microalbuminuria", a term which refers to the appearance of abnormal amounts of albumin in urine. Detection of microalbuminuria is generally used as a standard test for diagnosing DN. Whereas normoalbuminuria is typically defined by a urine albumin excretion rate (UAER) lower than 30 mg/24 h, microalbuminuria is defined by a urine albumin excretion rate comprised between 30 mg/24 h and 300 mg/24 h. The microalbuminuria stage may last about 10 years in patients. Then, the complication may progress to a "macroalbuminuria" stage, which is defined by a urine albumin excretion rate higher that 300 mg/24 h. Macroalbuminuria is generally indicative of overt DN and increased risk of ESRD. The urine albumin excretion rates and urine albumin creatinine ratios (UACR) associated with normo-, micro-, and macroalbuminuria are summarized in Table 1.

TABLE 1 urine albumin excretion rate (UAER) and urine albumin creatinine ratio (UACR) associated with normo-, micro-, and macroalbuminuria.

|  | Urine Albumin excretion rate (UAER) | | Urine Albumin creatinine ratio (UACR) | |
| --- | --- | --- | --- | --- |
|  | µg/min | mg/24 h | mg/mmol | mg/g |
| Normoalbuminuria | <20 | <30 | Men <2.5 Women <3.5 | <30 |
| Microalbuminuria | 20-200 | 30-300 | Men 2.5-25 Women 3.5-35 | Men 30-300 Women 30-400 |
| Macroalbuminuria | >200 | >300 | Men >25 Women >35 | Men >300 Women >400 |

The subject according the invention is normoalbuminuric, i.e. a normal amount of albumin may be detected in his/her urine. For instance, the urine albumin excretion rate (UAER) detected in the urine of said subject is lower than 20 µg/min, or than 30 mg/24 h. Alternatively, the urine albumin creatinine ratio (UACR) detected in the urine of said subject is lower than 2.5 mg/mmol if the subject is a woman, or lower than 3.5 mg/mmol if the subject is a man, or the UACR is lower than 30 mg/g.

Methods for determining the UAER or the UACR in a subject are well-known to the skilled person.

Therefore, the methods of the invention allow early prediction of an increased risk of diabetic nephropathy in a subject who does not present any symptoms of diabetic nephropathy, in particular who does not display microalbuminuria.

The present methods are based on the detection of particular proteins in a biological sample from a subject according to the invention.

The term "biological sample" refers to any type of biological sample. The biological sample may e.g. correspond to a urine sample, a blood sample, a serum sample or a plasma sample. The biological sample most preferably corresponds to a urine sample. The biological sample may optionally be treated for allowing further analysis of for example phosphorylated proteins, and such treatment may consist of using phosphatase inhibitors (for instance with 1 mM sodium orthovanadate, 10 mM sodium fluoride, 20 mM glycerol 2-phosphate disodium and/or protease inhibitors). Moreover, the biological sample may optionally be concentrated and/or frozen until use. In particular, the biological sample may be prepared as shown in Example 1.4.

According to a preferred embodiment, the biological sample comes from a subject who has been subjected to a "physical exercise" before sample collection. As used herein, a "physical exercise" or a "physical activity" is defined as any bodily movement produced by skeletal muscles requiring energy expenditure. For instance, the subject may have performed an exercise test on a cycle ergometer. To individualize the increment of exercise intensity during exercise test, the workload of each step may be calculated from the theoretical maximal aerobic power ($W_{max}$), i.e. power corresponding to the theoretical maximal oxygen consumption ($VO_{2max}$). In consequence, the subjects may undergo a test with the same relative incremental workload and may be compared at the same percentage of their $W_{max}$. The test may consist of six minutes steady-state workloads at 20, 40, 60 and of 80% $W_{max}$. The duration of the exercise may typically be around 24 minutes. The subjects may then rest and drink water before sample collection. In particular, the subject may have performed an exercise test as described in Example 1.2, or in O'Brien, Watts et al. (1995).

Biomarkers

The inventors have surprisingly found that a differential expression of certain particular proteins can be detected in biological samples from a subgroup of normoalbuminuric diabetic patients who have been determined to be at risk of developing diabetic nephropathy after a physical exercise test, and that this variation is associated with an increased risk of developing diabetic nephropathy.

These particular proteins, which may be used as biomarkers in the method for in vitro detection of an increased risk of diabetic nephropathy, are selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AMBP and zinc-alpha-2-glycoprotein.

Carbonic anhydrase 1 typically refers to the protein referenced as P00915 in the UniProtKB/Swiss-Prot database on Jan. 28, 2013. Alternative names for Carbonic anhydrase 1 include Carbonate dehydratase I, Carbonic anhydrase B, CAB, Carbonic anhydrase I, CA-I or CA1 (which herein means the protein encoded by the gene CA1), as non-limiting examples. Typically, carbonic anhydrase 1 is an enzyme that catalyzes the hydration of carbon dioxide and the dehydration of bicarbonate.

CD59 glycoprotein typically refers to the protein referenced as P13987 in the UniProtKB/Swiss-Prot database on Jan. 28, 2013. Alternative names for CD59 glycoprotein include 1F5 antigen, 20 kDa homologous restriction factor, HRF20, MAC-inhibitory protein, MAC-IP, MEM43 antigen, Membrane attack complex inhibition factor, MACIF, Membrane inhibitor of reactive lysis, MIRL, Protectin or CD59 (which herein means the protein encoded by the gene CD59), as non-limiting examples. Typically, CD59 glycoprotein is an inhibitor of the complement membrane attack complex (MAC) action. It binds to the C8 and/or C9 complements of the assembling MAC. CD59 is expressed by endothelial cells, including renal glomerular and peritubular endothelial cells.

Tetranectin typically refers to the protein referenced as P05452 in the UniProtKB/Swiss-Prot database on Jan. 28, 2013. Alternative names for Tetranectin include TN, C-type lectin domain family 3 member B, Plasminogen kringle 4-binding protein or CLEC3B (which herein means the protein encoded by the gene CLEC3B), as non-limiting examples. Typically, Tetranectin is a protein with a C-type lectin domain, which was originally isolated as a plasminogen-binding protein that can enhance plasminogen activation in the presence of tissue plasminogen activator.

Collagen alpha-1(I) chain typically refers to the protein referenced as P02452 in the UniProtKB/Swiss-Prot database on Jan. 28, 2013. Alternative names for Collagen alpha-1(I) chain include Alpha-1 type I collagen (which herein means the protein encoded by the gene COL1A1), as a non-limiting example. Typically, Collagen alpha-1(I) chain is a member of group I collagen (fibrillar forming collagen). Tough bundles of collagen called collagen fibers are a major component of the extracellular matrix that support most tissues and give cells structure from the outside, but collagen is also found inside certain cells.

Prothrombin typically refers to the protein referenced as P00734 in the UniProtKB/Swiss-Prot database on Jan. 28, 2013. Alternative names for Prothrombin include Coagulation factor II or F2 (which herein means the protein encoded by the gene F2), as non-limiting examples. Typically, Thrombin (F2a) is a key enzyme for blood coagulation and it is generated from prothrombin (F2) by proteolytic activation. Indeed, prothrombin is cleaved into the following 4 chains: activation peptide fragment 1, activation peptide fragment 2, thrombin light chain and thrombin heavy chain. The term "prothrombin or fragments thereof" is used to designate prothrombin, activation fragment 1, activation fragment 2, thrombin light chain or thrombin heavy chain.

Heparan sulfate proteoglycan core protein typically refers to the protein referenced as P98160 in the UniProtKB/Swiss-Prot database on Jan. 28, 2013. Alternative names for Heparan sulfate proteoglycan core protein include Basement membrane-specific heparan sulfate proteoglycan core protein, Perlecan, LC or HSPG2 (which herein means the protein encoded by the gene HSPG2), as non-limiting examples. Typically, Heparan sulfate proteoglycan core protein is a large multidomain proteoglycan that binds many extracellular matrix (ECM) components and cell-surface molecules. It is synthesized by both vascular endothelial and smooth muscle cells and deposited in the extracellular matrix. HSPG2 is cleaved into the following 2 chains: endorepellin (78 kDa) and LG3 peptide (22 kDa). Hereinafter, the term "heparin sulfate proteoglycan core protein or fragments thereof" is used to designate heparin sulfate proteoglycan core protein, endorepellin or LG3.

Mannan-binding lectin serine protease 2 typically refers to the protein referenced as O00187 in the UniProtKB/Swiss-Prot database on Jan. 28, 2013. Alternative names for Mannan-binding lectin serine protease 2 include MBL-associated serine protease 2, Mannose-binding protein-associated serine protease 2 or MASP2 (which herein means the protein encoded by the gene MASP2), as non-limiting examples. The alternate splice product of MASP2 is a protein of 185 amino acids and 20.62 kDa named MAp19 or sMAP (Small MBL-associated protein). Typically, Mannan-binding lectin serine protease 2 is a serum protease that plays an important role in the activation of the complement system via mannose-binding lectin. After activation by auto-catalytic cleavage it cleaves C2 and C4, leading to their activation and to the formation of C3 convertase. MASP2 is cleaved into the following 2 chains: mannan-binding lectin serine protease 2 A chain and mannan-binding lectin serine protease 2 B chain. In the present specification, the term "Mannan-binding lectin serine protease 2" indifferently designate MASP2 or Map19.

Alpha-1-antitrypsin typically refers to the protein referenced as P01009 in the UniProtKB/Swiss-Prot database on Jan. 28, 2013. Alternative names for Alpha-1-antitrypsin include Alpha-1 protease inhibitor, Alpha-1-antiproteinase or Serpin A1 (which herein means the protein encoded by the gene Serpin A1), as non-limiting examples. Typically, Alpha-1-antitrypsin is an inhibitor of serine proteases, and its primary target is neutrophil elastase, but it also has a moderate affinity for plasmin and thrombin. It is the major plasma inhibitor of FXIa and kallikreins.

Plasma serine protease inhibitor typically refers to the protein referenced as P05154 in the UniProtKB/Swiss-Prot database on Jan. 28, 2013. Alternative names for Plasma serine protease inhibitor include Acrosomal serine protease inhibitor, Plasminogen activator inhibitor 3, PAI-3, Protein C inhibitor, PCI, or Serpin A5 (which herein means the protein encoded by the gene Serpin A5), as non-limiting examples. Typically, Plasma serine protease inhibitor is a member of the serpin family of protease inhibitors. In humans, it is produced in the liver and secreted into the blood. It inhibits the proteases which comprise the protein C anticoagulant pathway, activated protein C and the thrombin-thrombomodulin complex.

Antithrombin-III typically refers to the protein referenced as P01008 in the UniProtKB/Swiss-Prot database on Jan. 28, 2013. Alternative names for Antithrombin-III include ATIII or Serpin C1 (which herein means the protein encoded by the gene Serpin C1), as non-limiting examples. Typically, Antithrombin-III is an important serine protease inhibitor in plasma, which regulates the blood coagulation cascade. It inhibits thrombin as well as factors IXa and Xa.

Alpha-enolase typically refers to the protein referenced as P06733 in the UniProtKB/Swiss-Prot database on Jan. 28, 2013. Alternative names for Alpha-enolase include 2-phospho-D-glycerate hydro-lyase, C-myc promoter-binding protein, Enolase 1, MBP-1, MPB-1, Non-neural enolase, NNE, Phosphopyruvate hydratase, Plasminogen-binding protein, or ENO1 (which herein means the protein encoded by the gene ENO1), as non-limiting examples. The alternate splice product of ENO1 is a protein of 341 amino acids and 36.92 kDa named MPB-1. In the present specification, the terms "Alpha-enolase" indifferently designate ENO1 and/or MPB-1.

Histone H2B type 1-O typically refers to the protein referenced as P23527 in the UniProtKB/Swiss-Prot database on Jan. 28, 2013. Alternative names for Histone H2B type 1-O include Histone H2B.2, Histone H2B.n, H2B/n, or HIST1H2BO (which herein means the protein encoded by the gene HIST1H2BO), as non-limiting examples.

Glutaminyl-peptide cyclotransferase typically refers to the protein referenced as Q16769 in the UniProtKB/Swiss-Prot database on Jan. 28, 2013. Alternative names for Glutaminyl-peptide cyclotransferase include Glutaminyl cyclase, QC, sQC, Glutaminyl-tRNA cyclotransferase, Glutamyl cyclase, EC, or QPCT (which herein means the protein encoded by the gene QPCT), as non-limiting examples. The alternate splice product of QPCT is a protein of 312 amino acids and 35.42 kDa named QPCT isoform 2. In the present specification, the term "Glutaminyl-peptide cyclotransferase" indifferently designates the QPCT protein defined above and/or the QPCT isoform 2.

Protein AMBP typically refers to the protein referenced as P02760 in the UniProtKB/Swiss-Prot database on Jan. 28, 2013. Alternative names for Protein AMBP include AMBP (which herein means the protein encoded by the gene AMBP), as a non-limiting example. Protein AMBP is cleaved into the following 3 chains: Alpha-1-microglobulin (alternative names: Protein HC, Alpha-1 microglycoprotein, or Complex-forming glycoprotein heterogeneous in charge), Inter-alpha-trypsin inhibitor light chain (alternative names: ITI-LC, Bikunin, EDC1, HI-30a, or Uronic-acid-rich protein) and Trypstatin. Hereinafter the term "Protein AMBP" is indifferently used to designate Protein AMBP, alpha-1-microglobulin, inter-alpha-trypsin inhibitor light chain and/or Trypstatin.

Zinc-alpha-2-glycoprotein typically refers to the protein referenced as P25311 in the UniProtKB/Swiss-Prot database on Jan. 28, 2013. Alternative names for Zinc-alpha-2-glycoprotein include Zn-alpha-2-GP, Zn-alpha-2-glycoprotein, or AZGP1 (which herein means the protein encoded by the gene AZGP1), as non-limiting examples.

It is understood that the measurement of a given protein in the method according to the present invention comprises the measurement of the protein naturally present in the concerned biological sample, which implies that it encompasses the measurement of the same protein having any potential post-translational modifications (such as glycosylation, phosphorylation, etc.) that may arise.

Methods for In Vitro Detection of an Increased Risk of Diabetic Nephropathy

The present invention concerns a method for the in vitro detection of an increased risk of diabetic nephropathy in a subject suffering from diabetes and being normoalbuminuric, said method comprising the steps of:

(a1) measuring the level of at least one protein selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AMBP and zinc-alpha-2-glycoprotein in a biological sample taken from the subject, and (b) determining from the level measured at step (a1) if said subject has an increased risk of developing diabetic nephropathy.

In a preferred embodiment, the method of the invention comprises the steps of:

(a1) measuring the level of at least one protein selected from the group consisting of heparan sulfate proteoglycan core protein or fragments thereof, carbonic anhydrase 1, prothrombin or fragments thereof, tetranectin, CD59 glycoprotein, plasma serine protease inhibitor, and mannan-binding lectin serine protease 2 or isoforms thereof in a biological sample taken from the subject, and (b) determining from the level measured at step (a1) if said subject has an increased risk of developing diabetic nephropathy.

In another embodiment, the method of the invention comprises the steps of:

(a1) measuring the level of at least one protein selected from the group consisting of heparan sulfate proteoglycan core protein or fragments thereof, carbonic anhydrase 1, prothrombin or fragments thereof, tetranectin, CD59 glycoprotein, plasma serine protease inhibitor, and mannan-binding lectin serine protease 2 or isoforms thereof in a biological sample taken from the subject, and measuring the level of at least one protein selected from the group consisting of antithrombin-III, alpha-1-antitrypsin, collagen alpha-1(I) chain, alpha-enolase, histone H2B type 1-O, glutaminyl-peptide cyclotransferase, protein AMBP and zinc-alpha-2-glycoprotein in a biological sample taken from the subject, and (b) determining from the levels measured at step (a1) if said subject has an increased risk of developing diabetic nephropathy.

Diabetic nephropathy (DN) is a glomerular pathology affecting about 25-40% of diabetic patients. Thus, among a population of diabetic patients, statistically about 25-40% of the subjects will develop diabetic nephropathy, while the remaining 60-75% of the subjects will never develop diabetic nephropathy. In order to be able to prevent the onset of the disease in patients that may develop diabetic nephropathy, it is desirable to evaluate the risk of a diabetic patient to develop diabetic nephropathy as early as possible, i.e. to predict the potential appearance of diabetic nephropathy in a diabetic patient before appearance of the first symptoms of diabetic nephropathy, for instance when diabetic patients are still normoalbuminuric.

"Detecting an increased risk of diabetic nephropathy in a subject suffering from diabetes" means predicting the appearance or development of diabetic nephropathy in said patient or evaluating the chance that said patient will suffer from diabetic nephropathy. "Detecting an increased risk of diabetic nephropathy in a subject suffering from diabetes" also means determining if said patient is likely to develop diabetic nephropathy.

"Measuring the level of at least one protein" means "measuring the expression level of at least one protein". This step may be performed using any method well-known in the art. For instance, the expression level of one or more proteins may be determined by gel electrophoresis, e.g. 2D gel electrophoresis. Electrophoresis may be coupled with mass spectrometry, for instance LC/MS-MS. The expression level of one or more proteins may also be directly determined by mass spectrometry, such as targeted mass spectrometry. The expression level of one or more proteins may also be determined by immunoblot assays, such as Western blots. Alternatively, the expression level of one or more proteins may be measured by immunological assays, such as ELISA, multiplex or antibody arrays. In particular, the expression level of one or more proteins may be measured as described in Examples 1.5, 1.10 and 1.11.

According to an embodiment, the level of several proteins may be measured in step a1) of the method of detection of an increased risk of diabetic nephropathy. Thus step a1) of the method may consist of measuring the levels of at least 2, 3, 4, 5, 6, 7, 8, 9, 10, 11, 12, 13, 14 or 15 proteins selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-0, glutaminyl-peptide cyclotransferase, protein AMBP and zinc-alpha-2-glycoprotein, preferably from the group consisting of heparan sulfate proteoglycan core protein or fragments thereof, carbonic anhydrase 1, prothrombin or fragments thereof, tetranectin, and CD59 glycoprotein. The levels of several proteins may be measured simultaneously or sequentially.

In a preferred embodiment, the method of the invention further comprises a step (a2) of comparing the level(s) measured at step (a1) with at least one pre-determined value and step (b) consists of determining the presence of an increased risk of diabetic nephropathy in the subject, based on the comparison in step (a2).

The term "pre-determined value" preferably refers to the average level of said at least one protein measured in a biological sample from normoalbuminuric subjects suffering from diabetes and determined not to be at risk of developing diabetic nephropathy.

In the context of the invention, the expression "normoalbuminuric subject" refers to subjects for whom UAER or UACR is as depicted in Table 1.

In the context of the invention, a subject is "determined not to be at risk of developing diabetic nephropathy" if no diabetic nephropathy has been clinically found in such subject after a period of at least 2 years of monitoring.

Alternately, such subjects determined not to be at risk of developing diabetic nephropathy are those normoalbuminuric subjects who remain normoalbuminuric after a physical exercise, as described in O'Brien, Watts et al., 1995 (Diabetes Care, Vol. 18, No. 12, December 1995). The use of the physical exercise to determine the absence of risk of developing diabetic nephropathy is particularly advantageous in the situations where the control subjects can with difficulty (or cannot) be monitored during a period of at least 2 years.

In another particular embodiment of the methods according to the invention wherein the levels of at least two proteins are determined, the level of a virtual marker, obtained from the levels of said at least two proteins as defined above, may be compared with at least one predetermined value. The use of a virtual marker for combining the results of at least two proteins is described, for instance, in US2013/0210661 (Bio-Rad Innovations and CNRS) and US2014004538 (Bio-Rad Innovations, CHRU Lille, and Université de Lille 2).

The predetermined value may be a threshold value, such as a median or mean, or a range of values, such as a confidence interval.

In particular, the predetermined value may correspond to the mean level of the protein in a population of diabetic individuals known to have no risk of diabetic nephropathy. The predetermined value may also correspond to the range of values of the level of the protein which is the most observed in a population of diabetic individuals known to have no risk of diabetic nephropathy.

The predetermined value may also correspond to the level of the at least one protein measured in a biological sample taken from the subject prior to the time of sampling of the biological sample in which said at least one protein is measured in step a1). For example, the predetermined value may be the level of said at least one protein in a sample taken from the subject at a time t0, whereas the level of the protein determined in step a1) is measured in a biological sample taken from the same subject at a time tx, wherein t0 and tx are different and tx is posterior to t0. The order of magnitude of the period A between tx and t0 (A=tx−t0) is preferably in months (preferably 24 months, still preferably 20 months, still preferably 18 months, still preferably 16 months, still preferably 14 months, still preferably 12 months, still preferably 11 months, still preferably 10 months, still preferably 9 months, still preferably 8 months, still preferably 7 months, still preferably 6 months, still preferably 5 months, still preferably 4 months, still preferably 3 months, still preferably 2 months, still preferably 1 month). More preferably, the order of magnitude of A is in weeks (preferably 6 weeks, more preferably 5 weeks, still preferably 4 weeks, still preferably 3 weeks, still preferably 2 weeks, still preferably one week). Still preferably, the order of magnitude of A is in days (preferably 45 days, more preferably 30 days, still preferably 25 days, still preferably 20 days, still preferably 18 days, still preferably 15 days, still preferably 12 days, still preferably 10 days, still preferably 8 days, still preferably 6 days, still preferably 5 days, still preferably 4 days, still preferably 3 days, still preferably 2 days and still preferably 1 day). Still preferably, the order of magnitude of A is in hours (preferably 72 hours, more preferably 60 hours, still preferably 48 hours, still preferably 36 hours, still preferably 24 hours, still preferably 18 hours, still preferably 12 hours, still preferably 10 hours, still preferably 8 hours, still preferably 6 hours, still preferably 4 hours, still preferably 3 hours, still preferably 2 hours, still preferably 1 hour). Still preferably, A is 90 minutes, still preferably 60 minutes, still preferably 45 minutes and still preferably 30 minutes. Preferably, t0 corresponds to the time of the sampling at the admission of the patient.

As known to the skilled person, the predetermined value is dependent on the biological sample type and on the method used for measuring the level of the protein in the biological sample. Thus, the predetermined value is preferably provided by using the same assay technique as used for measurement of the subject's protein levels, to avoid any error in standardization.

In particular, the method of the invention may further comprise a step a2) of determining whether the level(s) measured at step a1) is(are) higher or lower than at least one pre-determined value as defined above.

In the context of the invention, a level of a protein higher than, or lower than, a pre-determined value preferably refers to a level significantly higher than, or lower than, said pre-determined value in a statistic point of view.

In an embodiment, a decreased level of at least one protein selected from the group consisting of prothrombin or fragments thereof (in particular Activation peptide fragment 1), tetranectin, CD59 glycoprotein, plasma serine protease inhibitor, Map19, LG3, glutaminyl-peptide cyclotransferase, protein AMBP, alpha-enolase and histone H2B type 1-O in said subject is indicative of an increased risk of diabetic nephropathy. Preferably, a level of at least one protein selected from the group consisting of prothrombin or fragments thereof (in particular Activation peptide fragment 1), tetranectin, CD59 glycoprotein, plasma serine protease inhibitor, Map19, LG3, glutaminyl-peptide cyclotransferase, protein AMBP, alpha-enolase and histone H2B type 1-0 at least 10% lower than a pre-determined value is indicative of an increased risk of diabetic nephropathy or, according to increasingly preferred embodiments, at least 15%, 20%, 25%, 30%, 35%, 40%, 45%, 50%, 55%, 60%, 65%, 70%, 75%, 80%, 85%, 90%, 95% or 100% lower than a pre-determined value is indicative of an increased risk of diabetic nephropathy. More preferably, the level of at least one protein selected from the group consisting of prothrombin or fragments thereof (in particular Activation peptide fragment 1), tetranectin, CD59 glycoprotein, plasma serine protease inhibitor, Map19, LG3, glutaminyl-peptide cyclotransferase, protein AMBP, alpha-enolase and histone H2B type 1-O is statistically significantly decreased compared to a pre-determined value if the p-value is less than 0.05 in the appropriate statistical test.

In another embodiment, an increased level of at least one protein selected from the group consisting of endorepellin, carbonic anhydrase 1, collagen alpha-1(I) chain, alpha-1-antitrypsin, antithrombin-III and zinc-alpha-2-glycoprotein in said subject is indicative of an increased risk of diabetic nephropathy. Preferably, a level of at least one protein selected from the group consisting of endorepellin, carbonic anhydrase 1, collagen alpha-1(I) chain, alpha-1-antitrypsin, antithrombin-III and zinc-alpha-2-glycoprotein at least 10% higher than a pre-determined value is indicative of an increased risk of diabetic nephropathy, or according to increasingly preferred embodiments, at least 15%, 20%, 25%, 30%, 35%, 40%, 45%, 50%, 55%, 60%, 65%, 70%, 75%, 80%, 85%, 90%, 95% or 100% higher than a pre-determined value is indicative of an increased risk of diabetic nephropathy. More preferably, the level of at least one protein selected from the group consisting of endorepellin, carbonic anhydrase 1, collagen alpha-1(I) chain, alpha-1-antitrypsin, antithrombin-III and zinc-alpha-2-glycoprotein is statistically significantly increased compared to a pre-determined value if the p-value is less than 0.05 in the appropriate statistical test.

Another object of the invention pertains to a method for the prevention of diabetic nephropathy in a subject suffering from diabetes and being normoalbuminuric, said method comprising the steps of:

(a1) measuring the level of at least one protein selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AM BP and zinc-alpha-2-glycoprotein in a biological sample taken from the subject, (a2) optionally, comparing the level measured at step (a1) with at least one pre-determined value, (b) determining from the level measured at step (a1) or the comparison of step (a2) if said subject has an increased risk of developing diabetic nephropathy, and (c) if the subject has been determined at step (b) as having an increased risk of developing diabetic nephropathy, administering to said subject a preventive treatment against diabetic nephropathy.

In a preferred embodiment, the method for the prevention of diabetic nephropathy according to the invention comprises the steps of:

(a1) measuring the level of at least one protein selected from the group consisting of heparan sulfate proteoglycan core protein or fragments thereof, carbonic anhydrase 1, prothrombin or fragments thereof, tetranectin, CD59 glycoprotein, plasma serine protease inhibitor, and mannan-binding lectin serine protease 2 or isoforms thereof in a biological sample taken from the subject, and (a2) optionally, comparing the level measured at step (a1) with at least one pre-determined value, (b) determining from the level measured at step (a1) or the comparison of step (a2) if said subject has an increased risk of developing diabetic nephropathy, and (c) if the subject has been determined at step (b) as having an increased risk of developing diabetic nephropathy, administering to said subject a preventive treatment against diabetic nephropathy.

In another embodiment, the method for the prevention of diabetic nephropathy according to the invention comprises the steps of:

(a1) measuring the level of at least one protein selected from the group consisting of heparan sulfate proteoglycan core protein or fragments thereof, carbonic anhydrase 1, prothrombin or fragments thereof, tetranectin, CD59 glycoprotein, plasma serine protease inhibitor, and mannan-binding lectin serine protease 2 or isoforms thereof in a biological sample taken from the subject, and measuring the level of at least one protein selected from the group consisting of antithrombin-III, alpha-1-antitrypsin, collagen alpha-1(I), alpha-enolase, histone H2B type 1-O, glutaminyl-peptide cyclotransferase, protein AMBP and zinc-alpha-2-glycoprotein in a biological sample taken from the subject, and (a2) optionally, comparing the levels measured at step (a1) with at least one pre-determined value, (b) determining from the levels measured at step (a1) or the comparison of step (a2) if said subject has an increased risk of developing diabetic nephropathy, and (c) if the subject has been determined at step (b) as having an increased risk of developing diabetic nephropathy, administering to said subject a preventive treatment against diabetic nephropathy.

In the context of the invention, the term "preventive treatment against diabetic nephropathy" refers mainly to treatment with drugs that lower blood pressure by using anti-hypertensive agents such as, for instance, Angiotensin-converting enzyme (ACE) inhibitors or Angiotensin II receptor blockers (ARBs).

Method for the In Vitro Identification of a Marker for Prediction of Diabetic Nephropathy Another aspect of the present invention concerns a method for the in vitro identification of a marker for prediction of diabetic nephropathy, said method comprising the steps of:

(a) measuring the level of a protein in a biological sample taken from a subject suffering from diabetes who has been determined to be at risk of developing diabetic nephropathy, said biological sample being taken after said subject was subjected to a physical exercise as defined above, (b) measuring the level of said protein in a biological sample taken from a subject suffering from diabetes who has been determined not to be at risk of developing diabetic nephropathy, said biological sample being taken after said subject was subjected to a physical exercise as defined above, (c) comparing the level determined at step (b) with the level determined at step (a), and (d) identifying said protein as being a marker for prediction of diabetic nephropathy if the levels compared at step (c) are different.

The "method for in vitro identification of a marker" according to the invention may for instance be a method for in vitro screening of a marker.

As used herein, a "marker for prediction of a disease" detected in a biological sample from a subject refers to a biomolecule which expression level indicates that said disease is likely to appear, develop, or progress in said subject. Preferably, the marker for prediction is a protein. Preferably, the marker for prediction of a disease is an early marker, i.e. said marker allows early prediction of an increased risk of diabetic nephropathy in a subject who does not present any symptoms of diabetic nephropathy, including microalbuminuria.

Preferably, steps a) and b) of measuring the level of a protein may be carried out as described in the section "Method for in vitro detection of an increased risk of diabetic nephropathy" above.

The biological samples in steps (a) and (b) of the method of identification of a marker according to the invention are taken from the subjects after said subjects were subjected to a physical exercise, as described above.

The subject mentioned in step (a) of the present method has been determined to be at risk of developing diabetic nephropathy and the subject mentioned in step (b) of the present method has been determined not to be at risk of developing diabetic nephropathy.

"Determining if a subject is at risk, or respectively not at risk, of developing diabetic nephropathy" may be performed by any method well-known by the person skilled in the art. Preferably, this may be performed by submitting said subject to a physical exercise as described above. In particular, a subject may be determined to be at risk of developing diabetic nephropathy if he/she presents an increased level of urine albumin, a microalbuminuria, or a macroalbuminuria after a physical exercise as defined above. On the contrary, a subject who does not present an increased level of urine albumin, i.e. a subject remaining normalbuminuric after physical exercise as defined above, may be determined not to be at risk of developing diabetic nephropathy.

Step c) of the method of identification of a marker according to the invention consists of comparing the level determined at step (b) with the level determined at step (a), in other words determining if the level determined at step (b) and the level determined at step (a) are different. Preferably, the level determined at step (b) and the level determined at step (a) are considered as different if the difference between them is statistically significant. A statistically significant difference may, for instance, correspond to a p-value lower than 0.05 according to the appropriate statistical test.

If the levels thus compared at step (c) are different, preferably significantly different, then the protein which level has been measured in the biological samples is identified as being a marker for prediction of diabetic nephropathy.

Kits

A further object of the invention pertains to a kit comprising, in separate containers or in the same container, means for detecting at least two proteins selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AMBP and zinc-alpha-2-glycoprotein.

As used herein, the term "means for detecting at least one protein" refers to any means well-known by the person skilled in the art enabling detecting a protein or a peptide in a biological sample, in particular in a urine sample. For instance, means for detecting at least one protein may be one or more antibodies, preferably monoclonal antibodies.

Non-limiting examples of such means, in particular, antibodies for detecting heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I), glutaminyl-peptide cyclotransferase, protein AMBP, alpha-enolase, histone H2B type 1-O and/or zinc-alpha-2-glycoprotein are given in Table 4 (see Example 1.11). For instance, means for detecting CD59 glycoprotein, mannan-binding lectin serine protease 2, alpha-1-antitrypsin, antithrombin-III and carbonic anhydrase 1, glutaminyl-peptide cyclotransferase, protein AMBP, histone H2B type 1-O and zinc-alpha-2-glycoprotein may be, respectively, the antibodies provided by Sigma™ under the references HPA026494, SAB1401534, HPA001292, HPA001816, HPA006558, HPA008406, HPA001497, HPA043013 and HPA012582, means for detecting tetranectin, plasma serine protease inhibitor and heparan sulfate proteoglycan core protein may be, respectively, the antibodies provided by R&D Systems™ under the references µF5170, AF1266 and AF2364, and means for detecting prothrombin, collagen alpha-1(I) chain and alpha-enolase may be, respectively, the antibodies provided by Santa Cruz Biotechnology™ under the references sc-33769, sc-28657 and sc-15343.

The kit of the invention may also comprise one or more secondary antibodies conjugated to an enzyme or a fluorochrome. Alternatively, it may also comprise relevant combination of enzymes, metabolites and colorimetric or fluorescent substrates.

Preferably, the kit of the invention comprises means for detecting a combination of various biomarkers, as defined in the "Biomarkers" Section. For instance, the kit may comprise means for detecting at least 2, 3, 4, 5, 6, 7, 8, 9, 10, 11, 12, 13, 14 or 15 proteins selected from the group consisting of heparan sulfate proteoglycan core protein or fragments thereof, carbonic anhydrase 1, prothrombin or fragments thereof, tetranectin, CD59 glycoprotein, plasma serine protease inhibitor, mannan-binding lectin serine protease 2 or isoforms thereof, antithrombin-III, alpha-1-antitrypsin, collagen alpha-1(I) chain, alpha-enolase, histone H2B type 1-O, glutaminyl-peptide cyclotransferase, protein AMBP and zinc-alpha-2-glycoprotein.

The kit of the invention may also comprise other ingredients suitable for implementing certain techniques allowing detection of one or more proteins, such as e.g. immunoblotting techniques, immunostaining techniques, ELISA techniques, multiplex techniques, quantitative mass spectrometry, or antibody arrays, as non-limiting examples.

BRIEF DESCRIPTION OF THE FIGURES

FIGS. 4A-4B: Quantification of the Western-blot signals obtained for the analyzed biomarkers in urine samples of healthy subjects and diabetic patients suffering from nephropathy.

EXAMPLES

Figure 1:
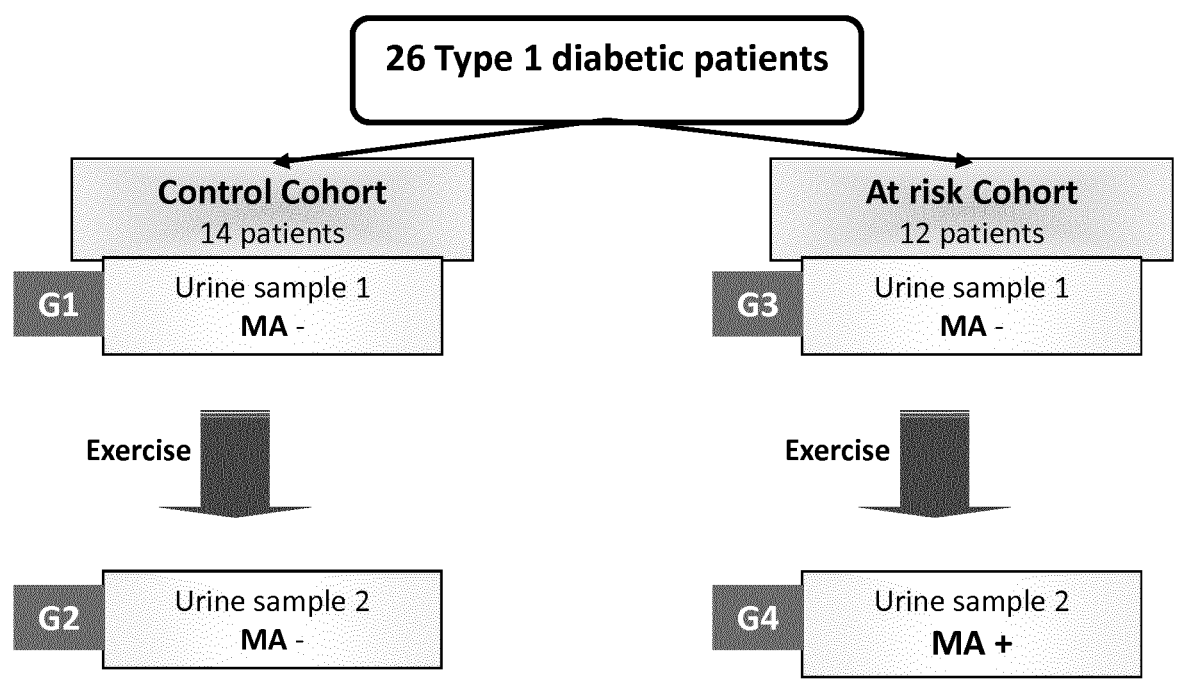
FIG. 1: Definition of the four groups of urine samples of diabetic patients.

Example 1: Materials and Methods 1.1. Recruitment of Patients

Twenty-six type 1 diabetic patients with a good glycemic control (all of them were equipped with an insulin pump) were recruited from patients of AMTIM in the Lapeyronie Hospital at Montpellier. The inclusion criteria were the following: type 1 diabetic patient with an average duration of diabetes of more than 5 years, no MA (defined as albumin/creatinine ratio (ACR)<30 mg/g). All patients gave written informed consent to participate in the study. The study was approved by regulatory authorities (approval of the Mediterranean Committee for the Protection of Persons, No. 2006-A00162-49).

1.2. Exercise Test and Urine Sample Collection

Patients were directed to the Central Service of Clinical Physiology, unit of metabolic exploration (CERAMM), Lapeyronie Hospital, Montpellier, France. At their arrival, mainly in the morning, the patients were given 200 ml of water every 20 min starting 1 h before the exercise test. The morning midstream clean-catch urine sample of each patient was collected just before starting the test. Then, all participants performed an exercise test on a cycle ergometer. To individualize the increment of exercise intensity during exercise test, the workload of each step was calculated from the theoretical maximal aerobic power ($W_{max}$), i.e., power corresponding to the theoretical maximal oxygen consumption ($VO_{2max}$). In consequence, the subjects underwent a test with the same relative incremental workload and were compared at the same percentage of their $W_{max}$. The test consisted of six-minute steady-state workloads at 20, 40, 60 and 80% of $W_{max}$. At the end of 24 minutes of exercise, all the patients rested for 1 hour and drank water. After this resting phase, the urine sample of each patient was collected. All urine samples were collected in sterile cups containing 1 mM sodium orthovanadate, 10 mM sodium fluoride, 20 mM glycerol 2-phosphate disodium (Sigma Aldrich, St. Louis, Mo.) and protease inhibitors (Roche Diagnostics, Meylan, France), and stored at −80° C. until use. Collection of urine samples was performed in a reproducible manner and in the same period.

1.3. Study Design

Urinary albumin/creatinine ratio (UACR) was determined for all samples before and after exercise test. Depending on UACR in samples collected after exercise test, the patients were divided into two cohorts: 1) a control cohort consisting of 14 patients whose urine remain negative for microalbuminuria (MA−) (UACR<30 mg/g) after the exercise test; and 2) a cohort considered at risk for developing DN consisting of 12 patients becoming positive for microalbuminuria (MA+) (30<UACR<300 mg/g) after the exercise test. The clinical characteristics of the patients are shown in Table 2.

TABLE 2

Clinical characteristics of type 1 diabetic patients.

| Clinical data | | Cohort | |
|---|---|---|---|
| | | Control | At risk |
| Number (n) | | 14 | 12 |
| Age (years) | | 48 ± 10.9 | 43.9 ± 10.4 |
| Sex (women/men) | | 8/6 | 8/4 |
| Duration of diabetes (years) | | 20.8 ± 7 | 19.6 ± 12 |
| Body mass index (kg/m2) | | 25.9 ± 4.1 | 23.06 ± 2.5 |
| HbA1C (%) | | 7.6 ± 1.2 | 7.1 ± 0.8 |
| Systolic blood pressure (mm Hg) | Before exercise | 124 ± 13 | 116 ± 13 |
| | After exercise | 171 ± 17 [b] | 182 ± 20 [b] |
| Diastolic blood pressure (mm Hg) | Before exercise | 86 ± 35 | 69 ± 9 |
| | After exercise | 76 ± 10 | 75 ± 9 |
| Creatinuria (g/L) | Before exercise | 0.46 ± 0.26 | 0.40 ± 0.32 |
| | After exercise | 0.31 ± 0.25 | 0.34 ± 0.29 |
| Albuminuria (mg/l) | Before exercise | 3.7 ± 2.2 | 4.5 ± 3.8 |
| | After exercise | 4.4 ± 6.5 | 48 ± 26.1 [a] [b] |
| UACR (mg/g) | Before exercise | 9 ± 4.6 | 13. ± 7.1 |
| | After exercise | 12.9 ± 7.2 | 178.6 ± 117.3 [a] [b] |

Values are expressed as mean ± S.D.
[a] P < 0.05 compared with control cohort;
[b] P < 0.05 compared with the same cohort after exercise test.

Thus, 4 different groups of urine samples were defined (FIG. 1):
- before the exercise test, the G1 group corresponds to samples collected from the control cohort and the G3 group collected from the cohort at risk; and
- after the exercise test, the G2 group corresponds to samples collected from the control cohort and the G4 group collected from the cohort at risk.

1.4. Urine Sample Preparation

Urine was centrifuged at 4° C. for 30 min at 11,000×g and the supernatant was dialyzed against 18 MΩ.cm water at 4° C. for 48 hours. Then, the sample was concentrated using 5000 Da cut-off centrifugal tube (Millipore, Bedford, Mass.) at 4° C. to approximately 1/40 of the initial volume. The concentrated urine was lyophilized and then solubilized in lysis buffer containing 8 M urea, 2 M thiourea, 4% w/v CHAPS, 65 mM DTE, 40 mM Tris-base and protease inhibitors for 2 h at room temperature on a rotating wheel. Protein amount was estimated using RCDC protein assay kit (Bio-Rad, Hercules, Calif.).

1.5. 2D-GE 18 cm long precast IPG strips with nonlinear immobilized pH 3-10 gradient were rehydrated with 170 μg of protein sample overnight in a solution containing 8 M urea, 2 Mthiourea, 4% w/v CHAPS, 65 mM DTE, 0.0025% v/v bromophenol blue and 1% v/v IPG buffer (3-10). Isoelectric focusing was carried out on the Ettan™ IPGphor™ isoelectric focusing system at 20° C. to a total amount of 50 kVh. After the first dimensional run, the proteins were reduced (6 M urea, 50 mM Tris-HCl, pH 8.8, 30% v/v glycerol, 2% w/v SDS, 0.001 v/v bromophenol blue and 65 mM DTT) and alkylated for 10 min in the same buffer containing 135 mM iodoacetamide instead of DTT. Then, proteins were separated in the second dimension on homemade 12% SDS-polyacrylamide gels using an ISO-DALT electrophoresis unit at a constant voltage of 120 V overnight at 10° C. The gels were stained with Sypro Ruby fluorescent dye (Bio-Rad, Hercules, Calif.).

1.6. Image Analysis

Gel images were digitalized individually with a Typhoon 9200™ scanner (GE Healthcare, Uppsala, Sweden) at 50 μm resolution with the photo multiplier tube (PMT) voltage adjusted for maximum range without signal saturation. Gel images were analyzed using Progenesis SameSpot software v3.0 (Nonlinear Dynamics, Durham, UK). Gels were warped to align images and protein spots were automatically detected. This software is based on the concept of recursive gel matching, which means that each gel of a matching set is recursively used as "reference gel" once during the matching process. The quality of the automatic match was critically evaluated in each case, and, if necessary, corrections were done manually.

1.7. Analysis of Data Quality

The Phylopuce method (Copois, Bibeau et al. 2007) was used to estimate the homogeneity of 2D-GE experiments so as to determine those of eventual bad quality. Briefly, each gel is represented by an expression vector of dimension n (n being the number of spots). The Euclidian distance between vectors (representing all experiments and their normalized spot intensities) was calculated. The resulting distance matrix was used to construct a phylogenetic tree using the "Kitsch algorithm". To visualize the obtained tree, the "Drawtree algorithm" which gives a graphical representation of an unrooted tree was used. This approach of classification based on distances between two dimensional gels establishes the overall homogeneity between gels and eventually pinpoints an experimental bias or the particular behavior of a sample.

1.8. Statistical Analysis

All statistics were computed with the "R/Bioconductor" statistical open source software (Gentleman, Carey et al. 2004). The differential intensity levels of protein spots between groups were analyzed using different statistical tests: Wlcoxon's test (Multtest package), Welch's test (Multtest package), VarMixt method (VarMixt package) and SAM method (siggenes package). With the multiple testing methodologies, it is important to adjust the p-value of each protein spot to control the False Discovery Rate (FDR). The Benjamini and Hochberg procedure (Benjamini 1995) was applied on all statistical tests and an adjusted p value less than 0.05 was considered as statistically significant. The AUC (area under the curve) ROC (receiver operating characteristic) was also calculated with the ROC package and an AUC ROC value greater than 0.75 was considered as significant.

For each significantly differential spot between two patient groups with one of the statistical tests used, a value was assigned to this spot according to Table 3. Thus all spots had a total score for all statistical tests between 0.5 and 5. Only spots with a score greater than or equal to 2 were included in the differential analysis.

TABLE 3

Value assigned to each statistical test and the total score for the spot

| Non adjusted test | | Adjusted test | | | | Other | Total |
|---|---|---|---|---|---|---|---|
| Wilcoxon | Welch | Wilcoxon | Welch | VarMixt | SAM | AUC | score |
| 0.5 | 0.5 | 0.5 | 0.5 | 1 | 1 | 1 | 5 |

1.9. In-Gel Digestion

Spots were excised from gels with a Propic robot (Perkin-Elmer, Wellesley, Mass.). All subsequent steps were done automatically using a Multiprobe II robot (Perkin-Elmer, Wellesley, Mass.). Spots were first washed with 300 µl of water and then 300 µl of 25 mM NH4HCO3. Destaining was performed twice in the presence of 300 µl of 50% acetonitrile in 25 mM NH4HCO3. Gel pieces were then dehydrated twice by 300 µl of 100% CH3CN, and finally dried at 37° C. for 1 h. Eight microliters of a trypsin solution (Sequencing Grade Modified Trypsin, Promega, Madison, Wis., USA), at a concentration of 0.0125 µg/µl in 25 mM NH4HCO3, was added to every spot and the samples were kept for 15 min first on ice and then at room temperature. Digestion was performed overnight at 37° C. and was stopped by addition of 2 µl of 2% formic acid. Digests were sonicated in an ultrasonic bath for 10 min and supernatants were transferred into HPLC polypropylene tubes.

1.10. Mass Spectrometry

The protein digests were analysed using a High Capacity ion trap mass spectrometer (Esquire HCT; Bruker Daltonik GmbH, Bremen, Germany), interfaced with a nano-HPLC Chip-Cube system (Agilent Technologies, Santa Clara, Calif., USA). The chips contained both the pre-column and the column (Zorbax 300SB-C18; Agilent Technologies, Santa Clara, Calif., USA). Samples were first loaded onto the 4 mm enrichment cartridge at a flow rate of 4 µl/min using 0.1% formic acid. After pre-concentration, peptides were separated on the column (75 µm diameter, 43 mm length) at a flow rate of 0.3 µl/min using a 15 min linear gradient from 3% to 80% acetonitrile in 0.1% formic acid, and eluted into the mass spectrometer. A capillary voltage of 1.8-2.1 kV in the positive ion mode was used together with a dry gas flow rate of 4.5 l/min at 250° C. A first full-scan mass spectrum was measured in the 310 m/z to 1800 m/z range, followed by a second scan at higher resolution to measure precisely the mass of the three major ions in the previous scan. Finally, a third scan was performed to acquire the collision-induced MS/MS spectra of the selected ions. MS/MS raw data were analyzed using Data Analysis software (Bruker Daltonik GmbH, Bremen, Germany) to generate the peak lists. The NCBI non-redundant database (NCBInr, release 20101018) was queried locally using the Mascot search engine (v. 2.2.04; Matrix Science, London, U.K.) with the following parameters: *Homo Sapiens* for the taxonomy, trypsin as enzyme, 1 missed cleavage allowed, carbamidomethylation of Cysteine as fixed modification, oxidation of Methionine as variable modification, and 0.6 Da mass accuracy in both MS and MS/MS. Under these conditions, individual ion scores above 40 indicated identity or extensive homology (p<0.05) and proteins were validated once they showed at least one peptide over this threshold.

1.11. Validation by Western Blotting

For Western blotting, 30 µg of each urine samples from the G1, G2, G3 and G4 groups (n=4, in each group) were resolved with SDS-PAGE at 160 V for approximately 2 h using SE260 mini-Vertical Electrophoresis Unit (GE Healthcare, Uppsala, Sweden). Then, proteins were transferred onto a nitrocellulose membrane and non-specific binding was blocked with 5% (w/v) skim milk in PBS-Tween 0.1% at 4° C. overnight. The membranes were then incubated with the appropriate primary antibodies (Table 4) at room temperature for 2 h. After washing, the membranes were further incubated with appropriate secondary antibodies anti-whole molecule IgG conjugated with horseradish peroxidase (Table 4) at room temperature for 1 h. Reactive protein bands were detected by enhanced chemiluminescence (ECL) (GE Healthcare, Uppsala, Sweden) using an autoradiogram.

TABLE 4

List of primary and secondary antibodies used for Western blotting

| Primary antibody anti- | Provider primary antibody | Reference | Concentration | HRP conjugated secondary antibody | Provider secondary antibody | Dilution |
|---|---|---|---|---|---|---|
| CA1 | Sigma | HPA006558 | 0.1 µg/ml | anti-rabbit IgG | Sigma | 1:150,000 |
| CD59 | Sigma | HPA026494 | 0.1 µg/ml | anti-rabbit IgG | Sigma | 1:150,000 |
| CLEC3B | R&D Systems | AF5170 | 0.2 µg/ml | anti-sheep IgG | Santa Cruz Biotechnology | 1:40,000 |
| COL1A1 | Santa Cruz Biotechnology | sc-28657 | 1 µg/ml | anti-rabbit IgG | Sigma | 1:150,000 |
| HSPG2 | R&D Systems | AF2364 | 0.2 µg/ml | anti-goat IgG | Sigma | 1:300,000 |
| F2 | Santa Cruz Biotechnology | sc-33769 | 1 µg/ml | anti-rabbit IgG | Sigma | 1:150,000 |

TABLE 4-continued

List of primary and secondary antibodies used for Western blotting

| Primary antibody anti- | Provider primary antibody | Reference | Concentration | HRP conjugated secondary antibody | Provider secondary antibody | Dilution |
|---|---|---|---|---|---|---|
| MASP2 | Sigma | SAB1401534 | 2 µg/ml | anti-rabbit IgG | Sigma | 1:150,000 |
| SERPIN A1 | Sigma | HPA001292 | 0.02 µg/ml | anti-rabbit IgG | Sigma | 1:150,000 |
| SERPIN A5 | R&D Systems | AF1266 | 0.2 µg/ml | anti-goat IgG | Sigma | 1:300,000 |
| SERPIN C1 | Sigma | HPA001816 | 1 µg/ml | anti-rabbit IgG | Sigma | 1:150,000 |

Example 2: Clinical Characteristics of Diabetic Patients and Proteomic Data Quality Based on the assumption that the appearance of microalbuminuria after exercise test is predictive of the onset of persistent MA after 10 years (O'Brien, Watts et al. 1995), the inventors have used a controlled exercise test to classify patients with type 1 diabetes in two cohorts: a cohort of control patients (14 patients remaining negative for MA after the exercise) and a cohort of patients at risk for DN (12 patients who became positive for MA after the exercise). For each cohort, urine samples were collected before (G1 and G3) and after (G2 and G4) exercise test (FIG. 1).

Clinical characteristics of the two cohorts of type 1 diabetic patients, control cohort and cohort at risk of developing DN, are described in Table 2. No significant differences were observed for age, duration of diabetes, systolic and diastolic blood pressure before exercise test, creatinuria and HbA1c among the two cohorts of patients. Compared with diabetic controls, diabetic subjects at risk of developing DN have higher levels of albuminuria and UACR after exercise test. The average level of systolic blood pressure was significantly higher after exercise than before for both cohorts.

The protein profiles of each urinary sample were studied by 2D-GE. After image analysis, 768 protein spots were visualized on each gel and the relative abundance of the protein spots was determined. The inter-experiment reproducibility was also assessed (average CV=19%).

Figure 2:
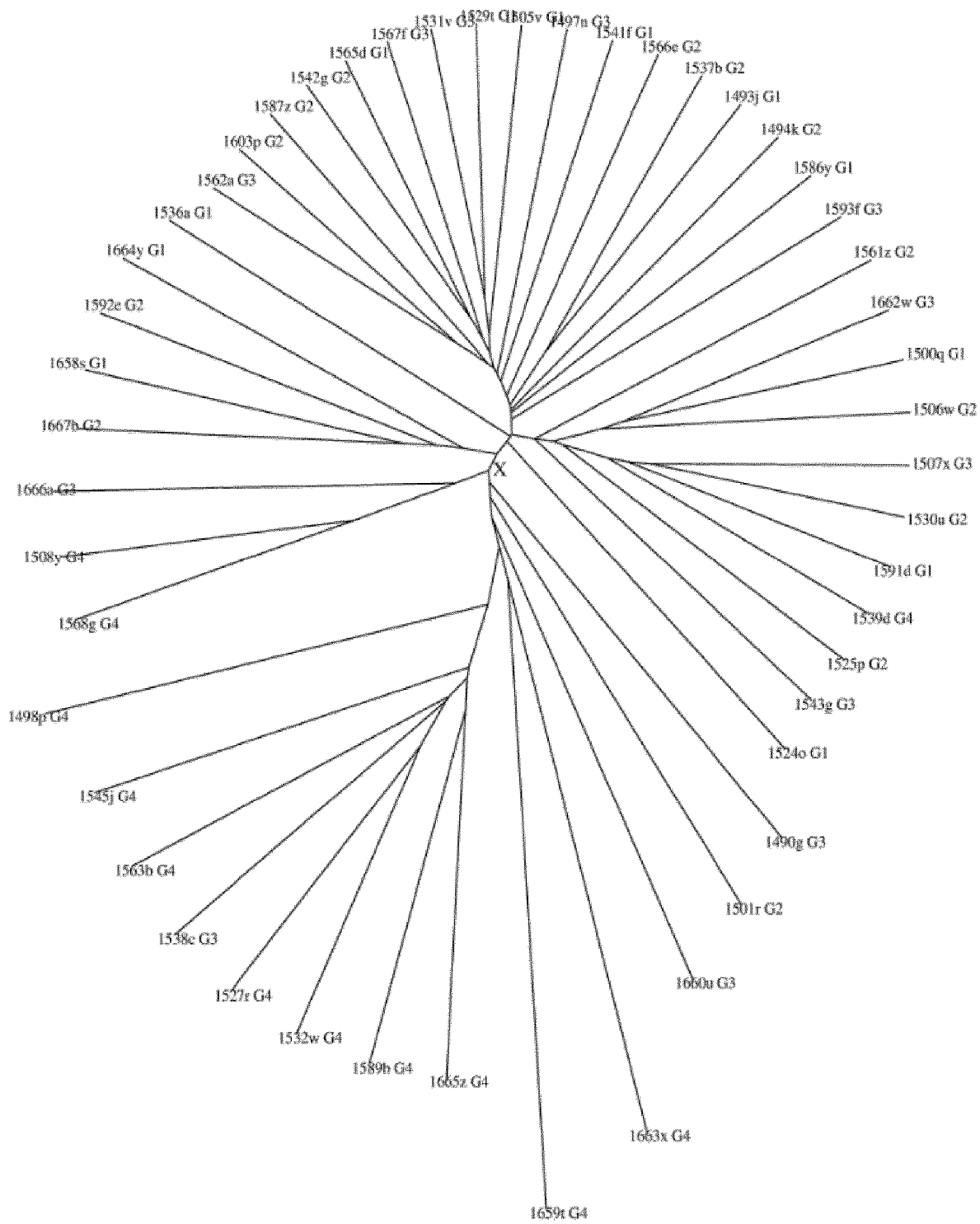
FIG. 2: Quality assessment of the series of 2D-GE experiments by a dispersion tree approach.

To evaluate the global quality of the 2D-GE data, the Phylopuce method was used to analyze the dispersion of experiments. This allows representing the series of experiments graphically in the form of an unrooted tree (FIG. 2). Ideally, a circle passing through all branches of the tree would reflect a perfect homogeneity of 2D gels. An analysis of the first results by Phylopuce showed that some gels were lying out from the remainder of the other gels (data not shown). By exploring the images of these distant gels, we noted a low quality due to bad migration of proteins with distortion and/or the presence of protein streaks. The samples corresponding to these gels were migrated again in 2D gels, which yielded to satisfactory quality 2D gel. The resulting unrooted tree in FIG. 2 shows an acceptable dispersion of the gels. Three of them behave, however, slightly differently, probably due to particular intrinsic properties of these samples and not to experimental problems since examination of these gels showed that they did not present apparent defects. It was decided to use all gels in further differential analysis.

Example 3: Comparative Analysis of Protein Expression

Urine samples were collected before and after exercise test from all patients from the two cohorts: control cohort (MA negative before and after exercise test) and at risk cohort (MA negative before test and MA positive after exercise test) yielding to four groups of urine, as described above.

Each group of urine samples (G1-G4) matched to a proteome of particular interest (Table 5) which can be revealed by differential analysis. Thus, the proteome profile of the G1 group (urine samples of control diabetic patients collected before the exercise test) contains all proteins shared between control type 1 diabetic patients. The proteome profile of the G2 group (urine samples of control diabetic patients collected after the exercise test) reflects all proteins whose urinary excretion was increased or decreased under the effect of physical activity among control patients. A set of proteins so-called "exercise proteome of control patients" is revealed by the comparison of protein profiles from urine samples of control patients collected before the exercise test (G1 group) with those collected from same patients after exercise (G2 group), i.e. the G1G2 comparison.

The G3 group (urine samples of diabetic patients at risk collected before exercise test) may include the candidate biomarkers for the early diagnosis of DN revealed without any physical activity. These biomarkers could be identified by comparing protein profiles from urine samples collected before the exercise test from control patients (G1 group) with those from at risk patients (G3 group), i.e. the G1G3 comparison.

The G4 group (urine samples of diabetic patients at risk for developing DN collected after exercise test) reflects biomarkers which are not differential before exercise test but become differential versus control after the exercise test. These biomarkers are revealed by the comparison of protein profiles from urine samples collected after the exercise test from control patients (G2 group) with those from at risk patients (G4 group), i.e. G2G4 comparison. The intersection of G2G4 comparison with G1G3 comparison reflects the candidate biomarkers for the early diagnosis of DN which are differential before and after exercise.

Furthermore, since it is collected after the exercise test, G4 group reflects "the exercise proteome of at risk patients". This proteome is highlighted by comparing the protein profiles of the urine samples collected from at risk patients before the exercise test (G3 group) with those collected from the same patients after exercise (G4 group), i.e. the G3G4 comparison.

TABLE 5

Each group of urine samples (G1-G4) and comparisons between them reflect a particular proteome and revealed biomarkers of DN

| Group | Reflection of | Comparison |
| --- | --- | --- |
| G1 | Proteins shared between control type 1 diabetic patients | — |
| G2 | The exercise proteome of control patients | G1G2 |
| G3 | Candidate biomarkers of DN before exercise test | G1G3 |
| G4 | Candidate biomarkers of DN only after exercise test | G2G4 |
|  | Candidate biomarkers of DN before and after exercise test | G2G4 ∩ G1G3 |
|  | The exercise proteome of at risk patients | G3G4 |

These four comparisons, G1G3, G2G4, G1G2 and G3G4, were performed to select potentially informative differences in protein expression. Several stringent criteria to select protein spots for further analysis were imposed. First, differences in protein expression were considered statistically significant if the total score calculated for each protein spot (representing the contribution of seven statistical tests) was greater than or equal to 2 (see Statistical analysis in the Materials and Methods section). Second, differential protein spots should be present in at least 50% of gels from one group compared to the other. Third, protein spots corresponding to albumin were eliminated (in G2G4 and G3G4 comparisons).

These analyses resulted in a total of 177 protein spots showing differential intensity. These protein spots derived from different comparisons, as follows.
For the detection of early DN biomarkers by comparing control cohort with at risk cohort:
before exercise test i.e. G1G3 comparison: 14 spots, including 8 up-regulated and 6 down-regulated in G3; and
after exercise test i.e. G2G4 comparison: 156 spots, including 104 up-regulated and 52 down-regulated in G4.
To identify the exercise proteome of controls and at risk diabetic patients, by comparing samples from the same cohort before and after exercise test:
in control cohort i.e. G1G2 comparison: 5 spots, including 2 up-regulated and 3 down-regulated in G2; and
in at risk cohort i.e. G3G4 comparison: 101 spots, including 72 up-regulated and 29 down-regulated in G4.

Overall, the number of differential protein spots between control cohort and at risk cohort was higher after exercise test (G2G4 comparison) than before (G1G3 comparison), suggesting that exercise has different effects on the protein urinary excretion in diabetic patients at risk for DN than in control patients. The G1G3 comparison reveals early candidate biomarkers DN between normoalbuminuric patients without performing the exercise test. Only three protein spots were specific of the G1G3 comparison; others were also found in G2G4, G3G4 and G1G2 comparisons. The exercise proteome of control patients appeared small (G1G2 comparison) with only 5 protein spots differentially expressed. At the opposite, the exercise proteome of at risk patients is more important with 101 differential spots expressed (G3G4 comparison).

There were some spots that overlap between the different comparisons. Four sets of differential spots which drew more attention were:

Set of 12 spots shared between the G1G3 and G2G4 comparisons. Therefore, these spots were differentially expressed between cohorts of control patients and at risk patients, before and after the exercise.

Set of 58 spots specific for the G2G4 comparison; they were differentially expressed between control patients and at risk patients after the exercise test.

Set of 38 spots specific for the G3G4 comparison; they were differentially expressed between the urine samples collected from at risk patients before and after the exercise test.

Graphs of statistical AUC ROC values of these sets of spots in the different comparisons show that most of the spots had AUC greater than 0.75. Interestingly, two protein spots were specific of G1G3 comparison, as two protein spots were specific of G1G2 comparison. Two other spots were shared between the G1G3, G2G4 and G3G4 comparisons. These spots as the set of 80 spots were part of candidate biomarkers as well as the exercise proteome of at risk patients, which explains their potential diagnostic interest.

Example 4: Identification of Differentially Expressed Proteins

The majority of spots that were significantly differential in all the comparisons were extracted from gels, digested with trypsin, and prepared for mass spectrometric (MS) analysis. These spots were identified by Nano LC-MS/MS. The total number of identified proteins was 73. All of these proteins were present in the DUP database constructed by the inventors (see Worldwide Website: sysdiag.cnrs.fr//index.php?page=dup), which contains more than 3000 non redundant urinary proteins described in the proteomic analysis of human normal urine in 19 publications (release 20110210).

From the statistical and functional analysis, 38 protein spots were selected which correspond to 24 different proteins identified by mass spectrometry. The expression level (up or down-regulated) and the molecular weight on 2D-GE of these 24 proteins are summarized in Table 6. All proteins are differentially expressed in post-exercise urine between at risk patients (G4 group) and that of control patients (G2 group). Carbonic anhydrase-1 (CA1), plasma protease C1 inhibitor (SERPING1), glutaminyl-peptide cyclotransferase (QPCT), protein AMBP, zinc-alpha-2-glycoprotein (AZGP1) and CD59 glycoprotein (CD59) are also differentially expressed in pre-exercise urine (G1G3 comparison). Endothelial protein C receptor (EPCR) is the only protein differentially expressed between pre-exercise urine of at risk patients (G3 group) and that of control patients (G1 group) (Table 6).

TABLE 6

Differentially expressed proteins in the 2D-GE comparison between control patients and at risk patients. Each protein was identified from one or several spots corresponding to a fragment or the full length of the protein and which are differential in one or more comparisons.

| Gene name | Theorical MW (kDa) | Spots | MW on 2D-GE (kDa) | G1G3/in G3 | G2G4/in G4 | G3G4/in G4 |
|---|---|---|---|---|---|---|
| EPCR | 27 | 717 | 36 | Down | | |
| CA1 | 29 | 817 | 31.5 | Up | Up | |
| | | 822 | 31.5 | Up | Up | |
| | | 825 | 31.5 | Up | Up | |
| | | 831 | 31.5 | Up | Up | |
| SERPING1 | 55 | 817 | 31.5 | Up | Up | |
| CD59 | 14.2 | 1009 | 21 | | Down | |
| | | 994 | 21 | | Down | Down |
| | | 1644 | 21 | | Down | Down |
| | | 1641 | 21 | | Down | Down |
| | | 1413 | 21 | Down | Down | Down |
| CLEC3B | 23 | 935 | 23 | | Down | |
| COL1A1 | 138 | 1331 | 60 | | Up | |
| F2 | 70/31 | 830 | 31 | | Down | |
| KLK3 | 29 | 784 | 30 | | Down | Down |
| | | 1551 | 22 | | Down | |
| SERPINA1 | 47 | 403 | 65 | | Up | |
| | | 414 | 65 | | Up | Up |
| | | 428 | 65 | | Up | |
| | | 433 | 65 | | Up | |
| | | 489 | 56 | | Up | |
| | | 1328 | 56 | | Up | |
| | | 1330 | 56 | | Up | |
| | | 1331 | 56 | | Up | |
| | | 1371 | 35 | | Up | |
| | | 1043 | 20 | | Down | |
| SERPINA5 | 46 | 537 | 55 | | Down | |
| SERPINC1 | 53 | 403 | 65 | | Up | |
| KLK1 | 30 | 592 | 45 | | Up | Up |
| MASP2 | 76 | 378 | 75 | | Up | Up |
| | | 966 | 22 | | | Down |
| | | 990 | 22 | | Down | |
| | | 1167 | 15 | | Down | |
| PLG | 91 | 1152 | 15 | | Down | |
| S100A8 | 11 | 1572 | 14.5 | | Down | Down |
| | | 1573 | 14.5 | | Down | |
| CD44 | 81.5 | 671 | 38 | | Up | |
| HSPG2 | 78 | 904 | 23.5 | | | Down |
| | | 1185 | 14.7 | | Down | |
| GNS | 62 | 499 | 55 | | Up | |
| | | 784 | 30 | | Down | Down |
| NID1 | 136 | 671 | 38 | | Up | |
| QPCT | 40 | 613 | 43.5 | | Up | |
| | | 630 | 42.4 | | | |
| | | 673 | 40 | Down | | |
| | | 1589 | 37.8 | | | |
| | | 1607 | 42 | | Down | |
| | | 1683 | 38.4 | Down | Down | |
| AMBP | 39 | 977 | 22 | Down | Down | |
| | | 1642 | 20.7 | | Down | |
| | | 994 | 21 | | Down | |
| | | 1004 | 20.7 | | Down | |
| | | 1009 | 20.6 | Down | Down | |
| | | 1413 | 21 | | Down | |
| | | 1456 | 35 | | Down | |
| | | 1457 | 35.4 | | Down | |
| | | 1461 | 34.5 | Up | | |
| | | 1641 | 21 | | Down | |
| ENO1 | 47 | 521 | 53.8 | | Down | |
| | | 537 | 52.8 | | Down | |
| AZGP1 | 34 | 410 | 65.5 | Up | Up | |
| | | 629 | 42.4 | Up | Up | |
| | | 674 | 40 | | Up | |
| | | 677 | 39 | | Up | |
| | | 1596 | 43.6 | Up | Up | |
| | | 1597 | 43.6 | | Up | |
| | | 411 | 65.3 | Up | Up | |
| | | 418 | 64.7 | Up | Up | |
| | | 550 | 50 | Up | Up | |
| | | 592 | 45.3 | Up | Up | |
| | | 616 | 43.4 | | Up | |

TABLE 6-continued

Differentially expressed proteins in the 2D-GE comparison between control patients and at risk patients. Each protein was identified from one or several spots corresponding to a fragment or the full length of the protein and which are differential in one or more comparisons.

| Gene name | Theorical MW (kDa) | Spots | MW on 2D-GE (kDa) | Comparison/up or down-regulated | | |
|---|---|---|---|---|---|---|
| | | | | G1G3/in G3 | G2G4/in G4 | G3G4/in G4 |
| | | 624 | 42.7 | | Up | |
| | | 626 | 42.6 | Up | Up | |
| | | 628 | 42.6 | | Up | |
| HIST1H2BO | 13 | 1440 | 17.9 | | Down | |

Example 5: Confirmation of Proteomic Analysis by Western-Blot Experiments on Treated and Concentrated Urine In order to validate the results obtained by 2D-GE approach and to verify the identities of proteins deduced from the results of LC-MS/MS analysis, the expression levels of 19 potential DN markers were analyzed by Western blotting.

Protein C inhibitor (SerpinA5), CD59 glycoprotein (CD59), tetranectin (CLEC3B) were decreased in G4 group in comparison with G2, confirming the proteomic data. Prothrombin or Coagulation factor II (F2) which has a molecular weight of 70 kDa is activated by a proteolytic cleavage, leading to formation of activation peptide fragments 1 and 2 (F1.2) (31 kDa), and active thrombin (F2a) (37 kDa). F1.2 is an index of in vivo thrombin generation, one molecule of F1.2 being released with the generation of each thrombin molecule. The antibody used was raised against amino-acids mapping near the N-terminus of F1.2. The 70 kDa of the prothrombin was increased in G4 group in comparison with G2, unlike the 31 kDa of cleaved F1.2 which was reduced in the same comparison. This suggests that the active thrombin is decreased in G4 group. Protein abundances of alpha-1-antitrypsin (SerpinA1), antithrombin-III (SerpinC1), carbonic anhydrase (CA1) and collagen alpha-1(I) chain (COL1A1) were higher in G4 group than in the G2 group. CA1, which has been also identified as differential between G1 and G3 groups, has not been confirmed by Western blotting since it was found in only 2 out of 4 samples of the G3 group. MASP2 and HSPG2 were later validated. A MASP2 fragment of around 20 kDa was decreased in G4 group in comparison with G2. HSPG2 is cleaved in 2 chains: Endorepellin and LG3 peptide. Endorepellin was higher in G4 group than in the G2 group and LG3 peptide was decreased in G4 group in comparison with G3 group.

Example 6: Confirmation of Proteomic Analysis by Western-Blot Experiments on Native Urine Following proteomic studies on 2D-GE, ten biomarkers were validated analytically (Western blot) on concentrated and treated urine.

The inventors investigated the presence of these biomarkers in samples of native urines (i.e. without previous treatment and unconcentrated).

First, 20 µL of each urinary sample were analyzed (total protein concentrations of the samples were variable (47.86 to 450.89 µg/ml)).

Among the ten biomarkers of interest, only the proteins HSPG2 (heparan sulfate proteoglycan 2), Col1A1 (Collagen, type I, alpha 1), Serpin C1 and F2 (prothrombin) were detected in Western blots on native urine.

Figure 3A:
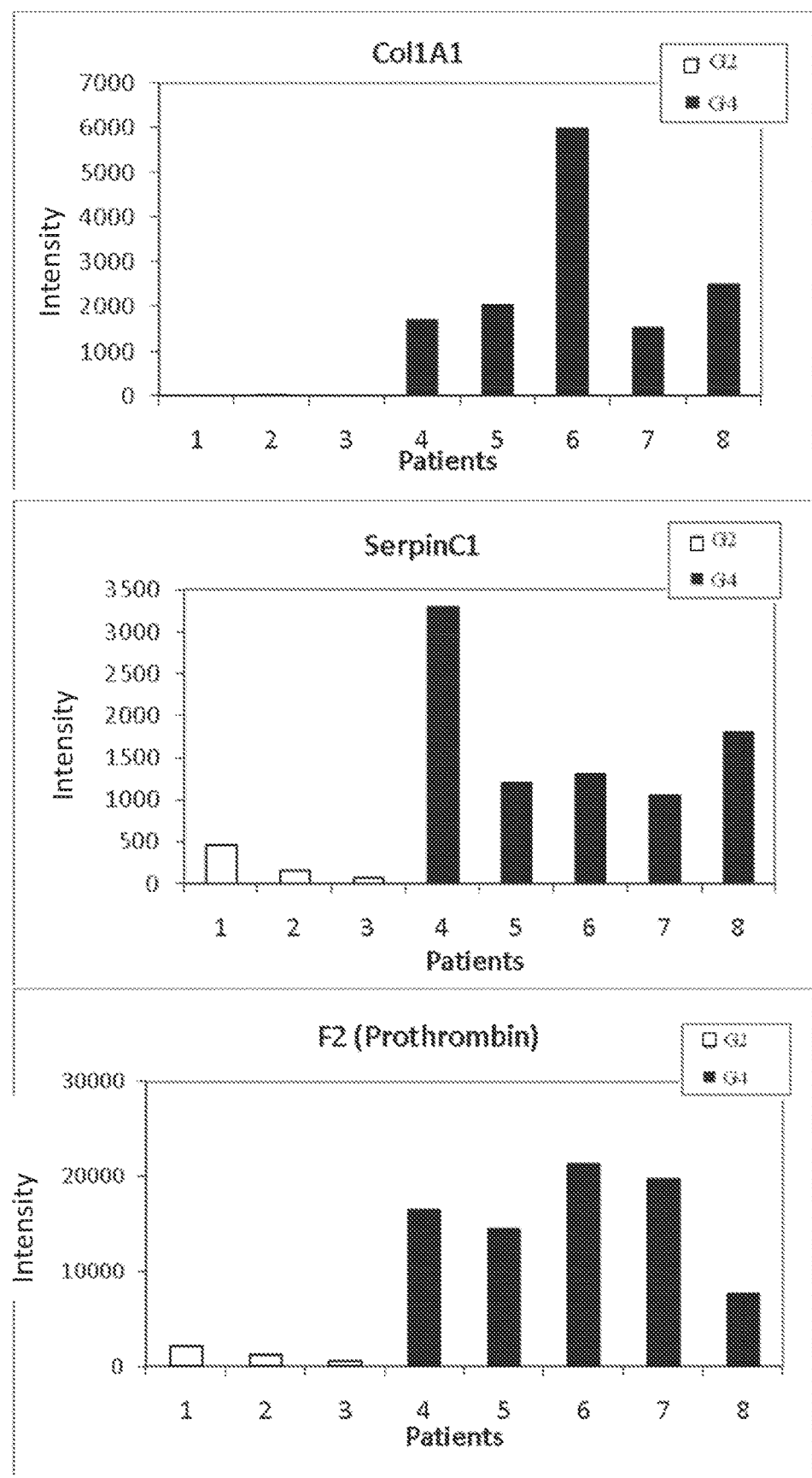
FIGS. 3A-3B: Quantification of the Western-blot signals obtained for the analyzed biomarkers in native urine samples of patients at risk of developing diabetic nephropathy (G4) and "control" patients (G2).
Figure 3B:
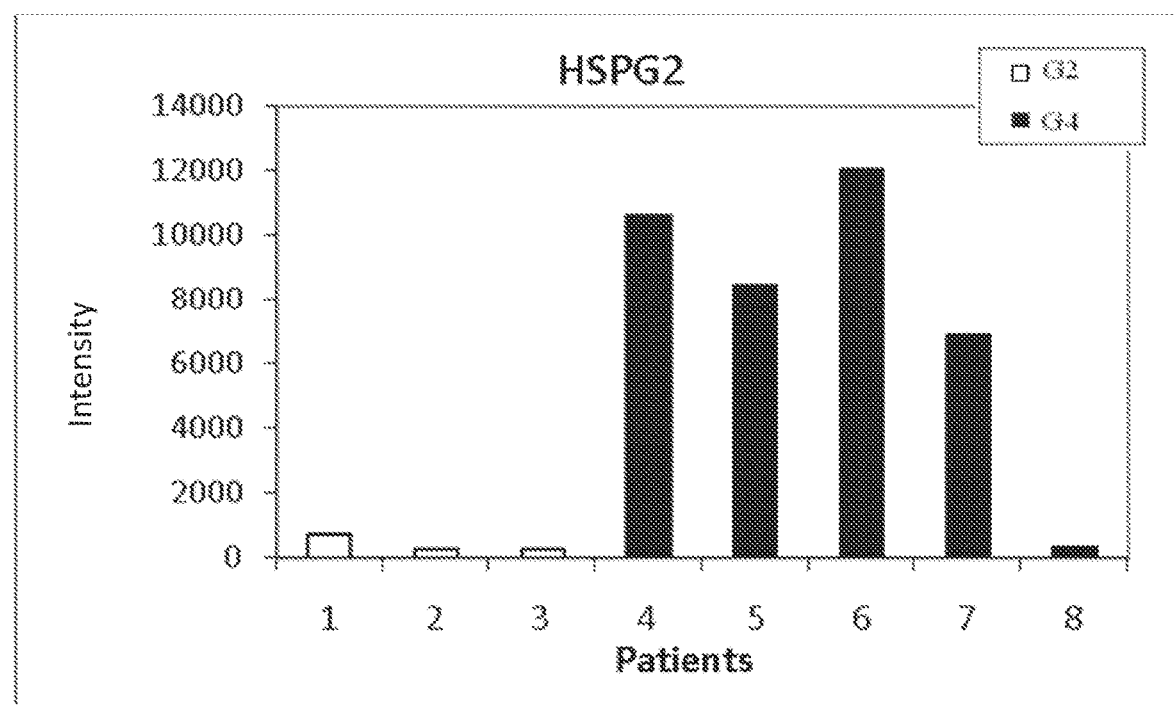

A relative quantification of these four biomarkers was performed on the same samples. An identical quantity of total proteins (1.6 µg) was loaded on SDS-PAGE gels. A same differential as that observed on treated urine was obtained (FIGS. 3A-3B). The four proteins were overexpressed in patients at risk of developing diabetic nephropathy (G4) in comparison to "control" patients (G2) (FIGS. 3A-3B).

Example 7: Confirmation of Proteomic Analysis by Western Blot Experiments on Urinary Samples from Healthy Subjects and Patients Suffering from Diabetic Nephropathy These ten biomarkers were selected as being specific of nephropathy and not of diabetes. In order to validate this point, analytic validation of the ten biomarkers was done for two other populations of subjects: i) healthy subjects who should behave as diabetic patients of the "control" cohort (G1, G2) and ii) diabetic patients suffering from nephropathy who should behave as diabetic patients of the "at risk" cohort (G3, G4).

Western blots were performed on urine from patients in these different groups.

Figure 4A:
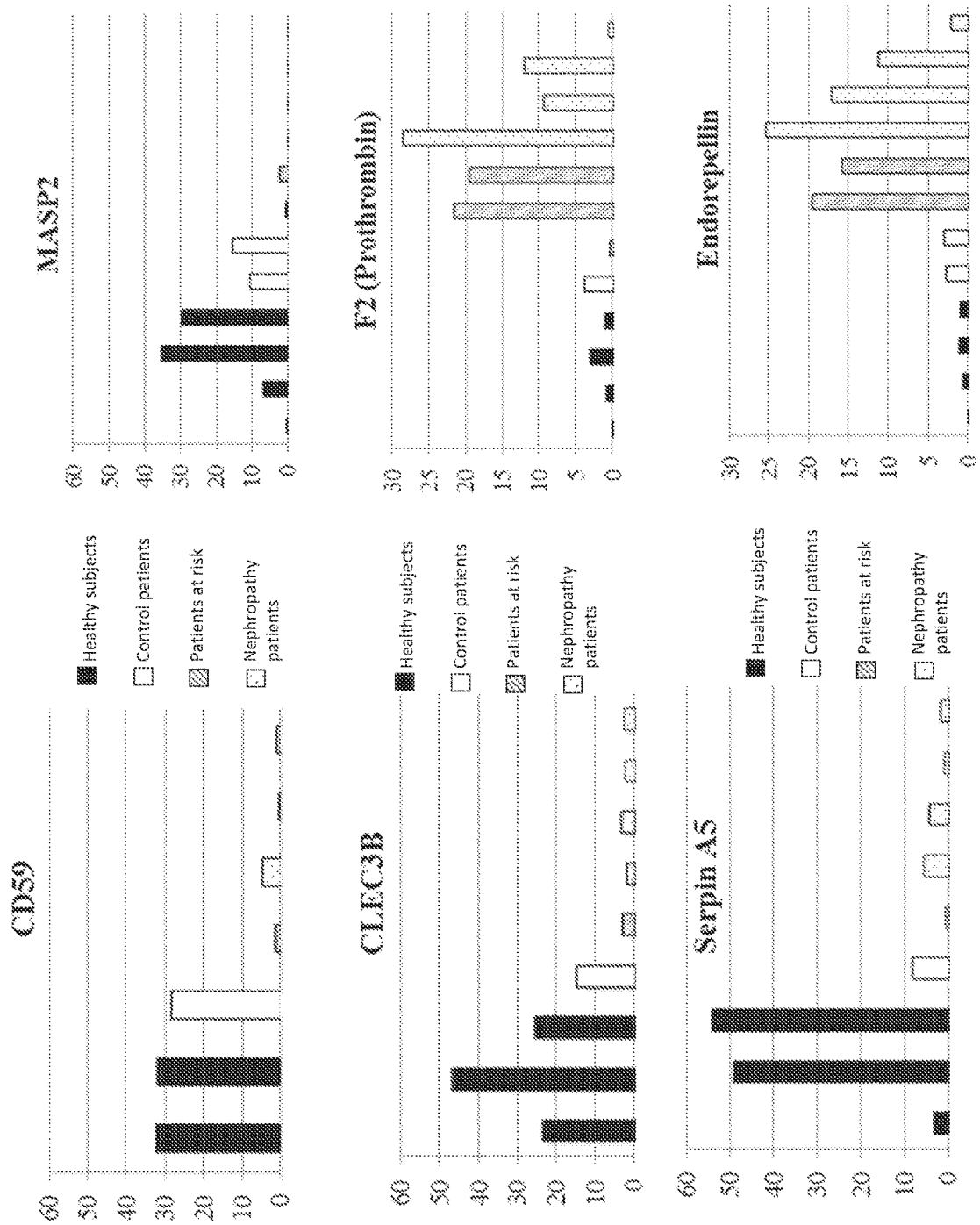

The proteins CD59, CLEC3B, Serpin A5, and MASP2 were under-expressed in urine of diabetic patients at risk of developing nephropathy and of diabetic patients suffering from nephropathy (microalbuminuric and macroalbuminuric patients) (FIGS. 4A-4B). Moreover, the protein MASP2 was not detected in urine from diabetic patients suffering from nephropathy (FIGS. 4A-4B). For certain biomarkers, the signals obtained for patients in the same group were not homogeneous. Indeed, concerning proteins Serpin A5 and MASP2, a healthy subject (different in both cases) appeared to have a lower quantity of analyzed biomarkers than the other studied healthy subjects.

The proteins HSPG2 and F2 were overexpressed in urine of diabetic patients at risk of developing diabetic nephropathy and in diabetic patients suffering from nephropathy (FIGS. 4A-4B). The signal obtained for a diabetic patient suffering from nephropathy was lower than for the other patients of the same group.

Six biomarkers were validated on two other cohorts of patients: CD59, CLEC3B, Serpin A5, MASP2, HSPG2 and F2.

The variations of protein expression were comparable between healthy subjects and patients of the "control" cohort, and between patients of the "at risk" cohort and diabetic patients suffering from nephropathy, showing that these six biomarkers are specific of nephropathy and not of diabetes.

Example 8: Diagnostic Performances of Single Marker or of Two-Marker Combinations The diagnostic performance of selected proteins according to the invention in the 2D-GE comparison between 5 control patients and at risk patients of developing diabetic nephropathy before physical exercises (G1 versus G3) was evaluated using a Receiving Operating Characteristics (ROC) analysis (Table 7). ROC curves are the graphical visualization of the reciprocal relation between the sensitivity (Se) and the specificity (Sp) of a test for various values.

TABLE 7

Examples of diagnosis performances of single marker for G1 versus G3 comparison.

| Markers | AUC ROC | Threshold | Sp (%) | Se (%) | VPP (%) | VPN (%) | CI 95% |
|---|---|---|---|---|---|---|---|
| CA1 | 0.875 | 10933795 | 83.3 | 91.7 | 84.6 | 90.9 | [0.713; 1.000] |
| CD59 | 0.792 | −138077543 | 91.7 | 75.0 | 90.0 | 78.6 | [0.583; 1.000] |
| AMBP | 0.771 | −14365141 | 91.7 | 66.7 | 88.9 | 73.3 | [0.567; 0.975] |
| QPCT | 0.764 | −5589612 | 83.3 | 75.0 | 81.8 | 76.9 | [0.560; 0.968] |

AUC ROC: area under the ROC curve; Threshold: expressed in 2D-GE relative intensity and selected by Youden index; Se: sensibility; Sp: specificity; PPV: positive predictive value (measures the proportion of subjects with positive test results who are correctly diagnosed); NPV: negative predictive value (measures the proportion of subjects with negative test results who are correctly diagnosed); CI 95%: 95% confidence interval.

Figure 5:
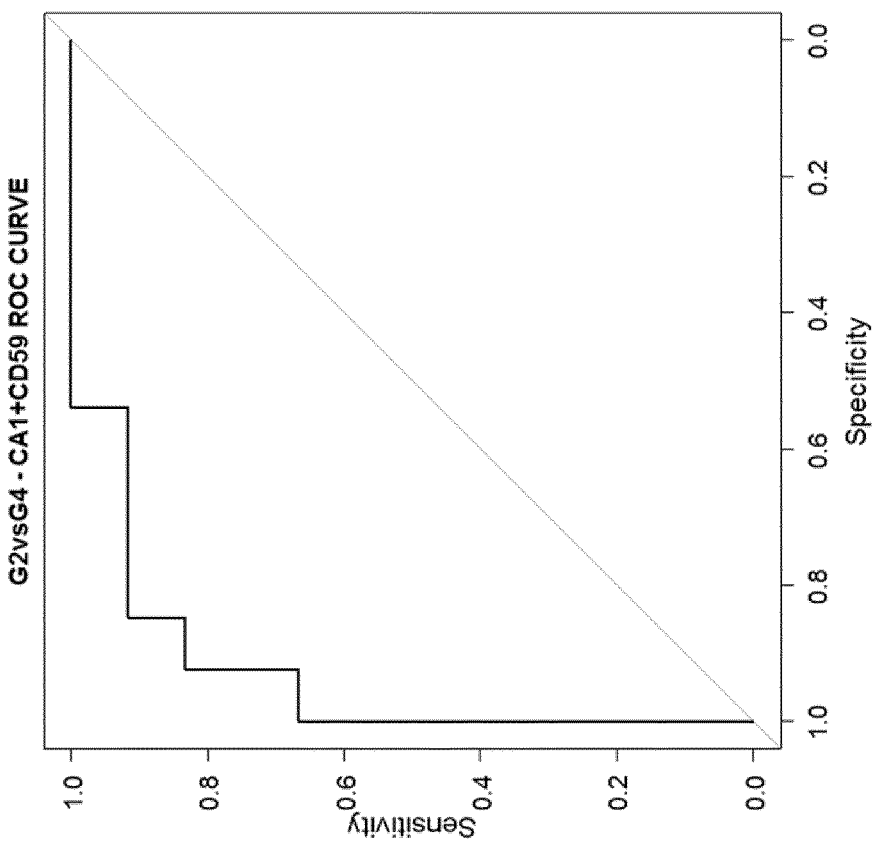
FIG. 5: ROC curves of CA1+CD59 combination (mROC method) for G1 versus G3 and G2 versus G4 comparison.
Figure 5:
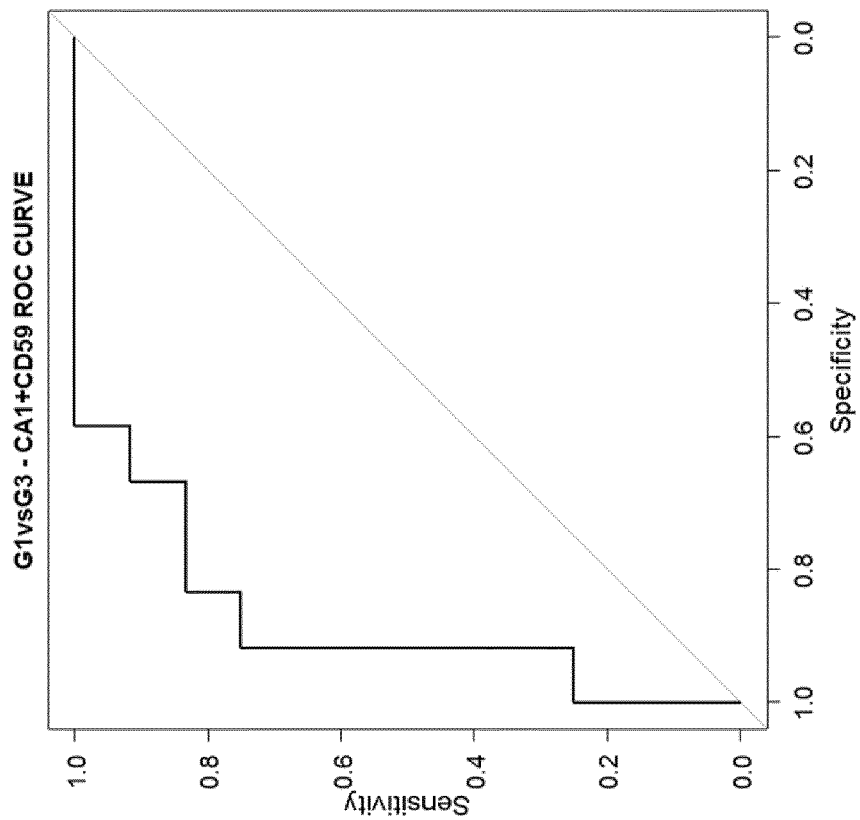

Multivariate analysis with mROC approach improved significantly AUC when comparing control patients versus at risk patients of developing diabetic nephropathy before physical exercises. The marker combination associating for example CA1 to CD59, CA1 to AMBP, CA1 to QPCT, CD59 to QPCT, and CD59 to AMPBP has a predictive value for higher risk of developing diabetic nephropathy as reported by the higher sensitivity and specificity (Table 8). The statistical analysis combining two markers generated a series of decision rules; a new virtual marker (Z) was calculated for each combination as illustrated in Table 9 and FIG. 5. Based on the combination of two markers, the virtual marker, transposing markers from the multivariate conditions into a univariate setting, discriminated significantly control patients from at risk patients of developing diabetic nephropathy before physical exercises with p-values<0.01.

TABLE 8

Examples of diagnosis performances (mROC approach) of two-markers combination for G1 versus G3 comparison.

| Markers combinations | AUC ROC | Threshold | Sp (%) | Se (%) | VPP (%) | VPN (%) | CI 95% |
|---|---|---|---|---|---|---|---|
| CA1 + CD59 | 0.882 | −0.2256 | 83.3 | 83.3 | 83.3 | 83.3 | [0.738; 1.000] |
| CA1 + AMBP | 0.931 | 0.9028 | 100.0 | 75.0 | 100.0 | 80.0 | [0.835; 1.000] |
| CA1 + QPCT | 0.917 | −0.4629 | 75.0 | 100.0 | 80.0 | 100.0 | [0.807; 1.000] |
| CD59 + QPCT | 0.847 | −3.5075 | 83.3 | 75.0 | 81.8 | 76.9 | [0.691; 1.000] |
| CD59 + AMBP | 0.833 | −2.7376 | 66.7 | 100.0 | 75.0 | 100.0 | [0.663; 1.000] |

AUC ROC: area under the ROCcurve; Threshold: expressed in 2D-GE relative intensity and selected by Youden index; Se: sensibility; Sp: specificity; PPV: positive predictive value (measures the proportion of subjects with positive test results who are correctly diagnosed); NPV: negative predictive value (measures the proportion of subjects with negative test results who are correctly diagnosed); CI 95%: 95% confidence interval.

TABLE 9

Examples of $a_1$ and $a_2$ coefficients maximizing AUC of ROC curve for two-markers combination (mROC approach).

| Markers combinations | Z = $a_1$ x [Marker1] + $a_2$ x [Marker2] |
|---|---|
| CA1 + CD59 | Z = +(1.56361513356411e−07)x[CA1] − (1.01677256583679e−08)x[CD59] |
| CA1 + AMBP | Z = +(1.35230449215072e−07)x[CA1] − (4.18637841481153e−08)x[AMBP] |
| CA1 + QPCT | Z = +(1.24848530852367e−07)x[CA1] − (9.75979899375066e−07)x[QPCT] |
| CD59 + QPCT | Z = −(1.36301781949143e−08)x[CD59] − (1.14127754739464e−06)x[QPCT] |
| CD59 + AMBP | Z = −(1.0745556660865e−08)x[CD59] − (3.39944153133327e−08)x[AMBP] |

The diagnostic performance of selected proteins according to the invention in the 2D-GE comparison between control patients and at risk patients of developing diabetic nephropathy after physical exercises (G2 verus G4) was evaluated using a Receiving Operating Characteristics (ROC) analysis (Table 10). ROC curves are the graphical visualization of the reciprocal relation between the sensitivity (Se) and the specificity (Sp) of a test for various values.

TABLE 10

Examples of diagnostic performances of single markers for G2 versus G4 comparison.

| Markers | AUC ROC | Threshold | Sp (%) | Se (%) | VPP (%) | VPN | CI 95% |
|---|---|---|---|---|---|---|---|
| CD59 | 0.891 | −116810836 | 92.3 | 91.7 | 91.7 | 92.3 | [0.723; 1.000] |
| AMBP | 0.872 | −9832649 | 100.0 | 83.3 | 100.0 | 86.7 | [0.696; 1.000] |
| AZGP1 | 0.872 | 22537171 | 92.3 | 83.3 | 90.9 | 85.7 | [0.718; 1.000] |
| CLEC3B | 0.872 | −4736752 | 69.2 | 100.0 | 75.0 | 100.0 | [0.733; 1.000] |
| HIST1H2BO | 0.872 | −12126916 | 92.3 | 83.3 | 90.9 | 85.7 | [0.719; 1.000] |
| F2 | 0.865 | −11964063 | 76.9 | 83.3 | 76.9 | 83.3 | [0.725; 1.000] |
| ENO1 | 0.840 | −1600077 | 69.2 | 91.7 | 73.3 | 90.0 | [0.677; 1.000] |
| MASP2 | 0.840 | −7360249 | 76.9 | 91.7 | 78.6 | 90.9 | [0.657; 1.000] |
| SERPINA1 | 0.808 | 12377059 | 100.0 | 58.3 | 100.0 | 72.2 | [0.633; 0.982] |
| HSPG2 | 0.801 | −11716038 | 84.6 | 75.0 | 81.8 | 78.6 | [0.616; 0.987] |
| QPCT | 0.795 | −1222240 | 69.2 | 83.3 | 71.4 | 81.8 | [0.602; 0.988] |
| CA1 | 0.776 | 15684748 | 92.3 | 75.0 | 90.0 | 80.0 | [0.559; 0.993] |
| SERPINA5 | 0.776 | −2657487 | 76.9 | 75.0 | 75.0 | 76.9 | [0.579; 0.973] |
| COL1A1 | 0.756 | 2727091 | 92.3 | 66.7 | 88.9 | 75.0 | [0.533; 0.980] |
| SERPINC1 | 0.724 | 1403159 | 38.5 | 100.0 | 60.0 | 100.0 | [0.521; 0.928] |

AUC ROC: area under the ROC curve; Threshold: expressed in 2D-GE relative intensity and selected by Youden index; Se: sensibility; Sp: specificity; PPV: positive predictive value (measures the proportion of subjects with positive test results who are correctly diagnosed); NPV: negative predictive value (measures the proportion of subjects with negative test results who are correctly diagnosed); CI 95%: 95% confidence interval.

Multivariate analysis with mROC approach improved significantly AUC when comparing control patients versus at risk patients of developing diabetic nephropathy after physical exercises. The marker combination associating for example CLE3B to ENO1, SERPINA5 to AZGP1, SERPINA5 to SERPINA1, and CLEC3B to CD59 has a predictive value for higher risk of developing diabetic nephropathy as reported by the higher sensitivity and specificity (Table 11). The statistical analysis combining two markers generated a series of decision rules; a new virtual marker (Z) was calculated for each combination as illustrated in Table 12 and FIG. 5. Based on the combination of two markers, the virtual marker, transposing markers from the multivariate conditions into a univariate setting, discriminated significantly control patients from at risk patients of developing diabetic nephropathy after physical exercises with p-values<0.001.

TABLE 11

Examples of diagnosis performances (mROC approach) of two-marker combination for G2 versus G4 comparison.

| Markers combinations | AUC ROC | Threshold | Sp (%) | Se (%) | VPP (%) | VPN (%) | CI 95% |
|---|---|---|---|---|---|---|---|
| CLEC3B + ENO1 | 0.994 | −9.8628 | 92.3 | 100.0 | 92.3 | 100.0 | [0.976; 1.000] |
| SERPINA5 + AZGP1 | 0.981 | −1.1267 | 100.0 | 91.7 | 100.0 | 92.9 | [0.938; 1.000] |

TABLE 11-continued

Examples of diagnosis performances (mROC approach) of two-marker combination for G2 versus G4 comparison.

| Markers combinations | AUC ROC | Threshold | Sp (%) | Se (%) | VPP (%) | VPN (%) | CI 95% |
|---|---|---|---|---|---|---|---|
| SERPINA1 + ENO1 | 0.974 | −2.0132 | 84.6 | 100.0 | 85.7 | 100.0 | [0.926; 1.000] |
| SERPINA5 + HIST1H2BO | 0.974 | −7.0219 | 100.0 | 91.7 | 100.0 | 92.9 | [0.920; 1.000] |
| COL1A1 + AZGP1 | 0.974 | 8.0182 | 92.3 | 91.7 | 91.7 | 92.3 | [0.926; 1.000] |
| CD59 + AZGP1 | 0.974 | 0.0539 | 84.6 | 100.0 | 85.7 | 100.0 | [0.926; 1.000] |
| CD59 + ENO1 | 0.968 | −5.8954 | 100.0 | 83.3 | 100.0 | 86.7 | [0.910; 1.000] |
| CLEC3B + HIST1H2BO | 0.962 | −4.2808 | 100.0 | 83.3 | 100.0 | 86.7 | [0.897; 1.000] |
| SERPINA5 + SERPINA1 | 0.955 | −2.5367 | 76.9 | 100.0 | 80.0 | 100.0 | [0.886; 1.000] |
| CA1 + ENO1 | 0.955 | −0.9247 | 84.6 | 100.0 | 85.7 | 100.0 | [0.883; 1.000] |
| F2 + ENO1 | 0.955 | −7.0566 | 84.6 | 91.7 | 84.6 | 91.7 | [0.886; 1.000] |
| CLEC3B + SERPINA5 | 0.949 | −6.0067 | 84.6 | 100.0 | 85.7 | 100.0 | [0.868; 1.000] |
| CLEC3B + CD59 | 0.942 | −3.8388 | 100.0 | 83.3 | 100.0 | 86.7 | [0.854; 1.000] |
| HSPG2 + ENO1 | 0.942 | −4.5482 | 76.9 | 100.0 | 80.0 | 100.0 | [0.858; 1.000] |
| SERPINA1 + AZGP1 | 0.942 | 4.5949 | 84.6 | 100.0 | 85.7 | 100.0 | [0.847; 1.000] |
| CLEC3B + QPCT | 0.942 | −4.4092 | 100.0 | 83.3 | 100.0 | 86.7 | [0.847; 1.000] |
| CD59 + AMBP | 0.942 | −4.1036 | 100.0 | 91.7 | 100.0 | 92.9 | [0.827; 1.000] |
| SERPINA5 + CD59 | 0.936 | −5.1362 | 76.9 | 100.0 | 80.0 | 100.0 | [0.847; 1.000] |
| CA1 + CD59 | 0.936 | −0.3404 | 84.6 | 91.7 | 84.6 | 91.7 | [0.843; 1.000] |
| CLEC3B + MASP2 | 0.936 | −4.51 | 92.3 | 91.7 | 91.7 | 92.3 | [0.840; 1.000] |

AUC ROC: area under the ROC curve; Threshold: expressed in 2D-GE relative intensity and selected by Youden index; Se: sensibility; Sp: specificity; PPV: positive predictive value (measures the proportion of subjects with positive test results who are correctly diagnosed); NPV: negative predictive value (measures the proportion of subjects with negative test results who are correctly diagnosed); CI 95%: 95% confidence interval.

TABLE 12

Examples of decision rules (mROC approach) for two-markers combination.

| Markers combinations | $Z = a_1 \times [\text{Marker1}] + a_2 \times [\text{Marker2}]$ |
|---|---|
| ENO1 + CLEC3B | $Z = -(2.69376695675031e-06) \times [\text{ENO1}] - (1.28313845176674e-06) \times [\text{CLEC3B}]$ |
| AZGP1 + SERPINA5 | $Z = +(7.60396312049394e-08) \times [\text{AZGP1}] - (1.05893383881848e-06) \times [\text{SERPINA5}]$ |
| SERPINA1 + ENO1 | $Z = +(1.05105404198974e-07) \times [\text{SERPINA1}] - (1.79201124674486e-06) \times [\text{ENO1}]$ |
| SERPINA5 + HIST1H2BO | $Z = -(1.34567451384797e-06) \times [\text{SERPINA5}] - (2.84140535140061e-07) \times [\text{HIST1H2BO}]$ |
| AZGP1 + COL1A1 | $Z = +(2.30613768688269e-07) \times [\text{AZGP1}] + (9.79281397114118e-07) \times [\text{COL1A1}]$ |
| AZGP1 + CD59 | $Z = +(1.7901623652807e-07) \times [\text{AZGP1}] - (2.03071085055857e-08) \times [\text{CD59}]$ |
| ENO1 + CD59 | $Z = -(1.86395627696331e-06) \times [\text{ENO1}] - (7.12337868208147e-08) \times [\text{CD59}]$ |
| CLEC3B + HIST1H2BO | $Z = -(6.50612939337824e-07) \times [\text{CLEC3B}] - (1.41763210039085e-07) \times [\text{HIST1H2BO}]$ |
| SERPINA1 + SERPINA5 | $Z = +(1.23367232406594e-07) \times [\text{SERPINA1}] - (1.19777770779838e-06) \times [\text{SERPINA5}]$ |
| ENO1 + CA1 | $Z = -(1.64889590005268e-06) \times [\text{ENO1}] + (9.36482853645907e-08) \times [\text{CA1}]$ |
| ENO1 + F2 | $Z = -(1.91161716055277e-06) \times [\text{ENO1}] - (2.67941736919358e-07) \times [\text{F2}]$ |
| SERPINA5 + CLEC3B | $Z = -(8.30972614812445e-07) \times [\text{SERPINA5}] - (8.11124364413926e-07) \times [\text{CLEC3B}]$ |
| CLEC3B + CD59 | $Z = -(4.95333344427748e-07) \times [\text{CLEC3B}] - (3.36932265360167e-08) \times [\text{CD59}]$ |
| ENO1 + HSPG2 | $Z = -(1.75495527888539e-06) \times [\text{ENO1}] - (7.28595572223807e-08) \times [\text{HSPG2}]$ |
| AZGP1 + SERPINA1 | $Z = +(2.04261743598041e-07) \times [\text{AZGP1}] + (3.2210138018648e-07) \times [\text{SERPINA1}]$ |
| CLEC3B + QPCT | $Z = -(7.04107016208075e-07) \times [\text{CLEC3B}] - (1.41762801540533e-06) \times [\text{QPCT}]$ |
| AMBP + CD59 | $Z = -(-9.84720704127077e-09) \times [\text{AMBP}] - (9.69931119857907e-08) \times [\text{CD59}]$ |
| SERPINA5 + CD59 | $Z = -(8.79594384945904e-07) \times [\text{SERPINA5}] - (6.90048286568996e-08) \times [\text{CD59}]$ |
| CA1 + CD59 | $Z = +(7.02229904137993e-08) \times [\text{CA1}] - (5.79940015439689e-08) \times [\text{CD59}]$ |
| CLEC3B + MASP2 | $Z = -(7.61697614199002e-07) \times [\text{CLEC3B}] - (4.24259818124178e-08) \times [\text{MASP2}]$ |

Example 9: Discussion

To search for early DN biomarker candidates in urine samples, 2D-GE analysis was performed, which is an accurate semi-quantitative comparison method to analyze differences between the urine proteomes from control and at risk patients. 14 and 156 protein spots that were differentially expressed before and after exercise test, respectively, were observed. The exercise proteomes of control and at risk diabetic patients were obtained by comparing the pre- and post-exercise test urine samples in each cohort (G1G2 and G3G4 comparisons, respectively). Greater variability of excreted urinary protein after the exercise in at risk patients (101 differential spots) than in control patients (5 differential spots) was observed.

Among proteins identified as potential DN markers, ten were validated by Western blotting. Many differential spots in G2G4 comparison have a statistical total score equal to 5, which means that their differences in protein expression are statistically very significant (in the seven statistical tests). These proteins thus have a potential clinical diagnostic value.

The invention claimed is:

1. A method for identifying risk of developing diabetic nephropathy in a normoalbuminuric diabetic and treating comprising:
    (a) obtaining a urine sample from a normoalbuminuric diabetic subject, wherein the subject is capable of developing microalbuminuria after a physical exercise test,
    (b) measuring the protein expression level of carbonic anhydrase 1 in the urine sample,
    (c) identifying the normoalbuminuric diabetic subject of step (a) at increased risk of developing diabetic nephropathy when the protein expression level of carbonic anhydrase 1 is at least 10% higher than a pre-determined value,
    wherein the predetermined value is a level of the carbonic anhydrase 1 protein measured in a urine sample obtained from a control normoalbuminuric diabetic subject suffering from diabetes and determined not to be at risk for diabetic nephropathy by either absence of microalbuminuria after the physical exercise test or absence of clinical symptoms for at least 2 years; and
    (d) administering drugs that lower blood pressure to the identified subject of (c), wherein the drugs are selected from angiotensin-converting enzyme (ACE) inhibitors or angiotensin II receptor blockers (ARBs).

2. The method according to claim 1, wherein said normoalbuminuric diabetic subject has type-1 or type-2 diabetes.

3. The method according to claim 1, wherein said measuring the expression level of step (b) comprises gel electrophoresis, 2D gel electrophoresis, mass spectrometry, or an immunological assay to determine the expression level of carbonic anhydrase 1.

4. The method according to claim 3, wherein said mass spectroscopy is targeted mass spectroscopy or LC/MS-MS.

5. The method according to claim 3, wherein said immunological assay is an ELISA, a multiplex immunoassay or an antibody array.

6. The method according to claim 1, said method further comprising:
    obtaining a second urine sample from the normoalbuminuric diabetic subject, said urine sample being taken from the subject after a physical exercise test.

7. The method according to claim 6, wherein the exercise test comprises a cycle ergometer.

* * * * *